US009592080B2

(12) United States Patent
Bagnasco et al.

(10) Patent No.: US 9,592,080 B2
(45) Date of Patent: *Mar. 14, 2017

(54) ORTHOPAEDIC DEVICE FOR CORRECTING DEFORMITIES OF LONG BONES

(71) Applicant: ORTHOFIX S.R.L., Bussolengo (Verona) (IT)

(72) Inventors: Mara Bagnasco, Milan (IT); Daniele Venturini, Povegliano Veronese (IT); Graziano Marini, Castel d'Azzano (IT)

(73) Assignee: ORTHOFIX S.R.L., Bussolengo (Verona) (IT)

( * ) Notice: Subject to any disclaimer, the term of this patent is extended or adjusted under 35 U.S.C. 154(b) by 166 days.

This patent is subject to a terminal disclaimer.

(21) Appl. No.: 14/617,542

(22) Filed: Feb. 9, 2015

(65) Prior Publication Data
US 2015/0150600 A1 Jun. 4, 2015

Related U.S. Application Data

(63) Continuation of application No. 13/063,510, filed as application No. PCT/IB2009/006735 on Sep. 14, 2009, now Pat. No. 8,951,253.

(30) Foreign Application Priority Data

Sep. 16, 2008 (IT) .............................. BO2008A0565

(51) Int. Cl.
*A61B 17/64* (2006.01)
*A61B 17/66* (2006.01)
*A61B 17/00* (2006.01)
(52) U.S. Cl.
CPC .......... *A61B 17/6483* (2013.01); *A61B 17/66* (2013.01); *A61B 2017/00398* (2013.01)

(58) Field of Classification Search
CPC ................ A61B 17/6483; A61B 17/66; A61B 2017/00398
(Continued)

(56) References Cited

U.S. PATENT DOCUMENTS 2,251,209 A 7/1941 Stader
4,312,336 A 1/1982 Danieletto et al.
(Continued)

FOREIGN PATENT DOCUMENTS

EP 0858781 A2 8/1998
FR 2705881 A1 12/1994
WO 2006102168 A2 9/2006

OTHER PUBLICATIONS

International Search Report, PCT/IB2009/006735, dated Dec. 11, 2009, 2 pages.
(Continued)

*Primary Examiner* — Mary Hoffman
*Assistant Examiner* — David C Comstock
(74) *Attorney, Agent, or Firm* — Baker & McKenzie LLP

(57) ABSTRACT

Orthopedic device (10, 110, 210, 310) for correcting deformities of a long bone (11), comprising a bar (12), extended along an axis (Y-Y) and intended to be placed alongside the bone (11), at least a first clamp (14, 214, 314) for a first group of osseous screws (16) and a second clamp (18, 19, 118) for a second group of osseous screws (20, 22), removably mounted on said bar (12), wherein the first of said clamps (14, 214, 314) is placed onboard a support base (21, 221, 321) in turn mounted on said bar (12), and angularly movable in relation to the support base around a given rotation axis (X-X, X'-X', Z-Z) by means of a rotary coupling, characterized in that said rotary coupling comprises a male element (35; 235, 236, 237, 238, 239; 333, 334) associated with the first clamp (14, 214, 314) and having a
(Continued)

surface at least partially cylindrical, and a corresponding female element (36; 130; 250, 254, 255; 336, 337) associated with the support base (21, 221, 321) and having a surface at least partially cylindrical constituting a seat for the loose coupling of the male element (35; 235, 236, 237, 238, 239; 333, 334).

16 Claims, 23 Drawing Sheets

(58) Field of Classification Search
USPC .............................. 606/53–59, 105, 282, 90
See application file for complete search history.

(56) References Cited

U.S. PATENT DOCUMENTS

| | | | |
|---|---|---|---|
| 4,488,542 A | 12/1984 | Helland | |
| 4,988,349 A | 1/1991 | Pennig | |
| 5,108,394 A | 4/1992 | Kurokawa et al. | |
| 5,167,661 A | 12/1992 | Wagenknecht | |
| 5,320,623 A | 6/1994 | Pennig | |
| 5,709,681 A | 1/1998 | Pennig | |
| 5,902,302 A | 5/1999 | Berki et al. | |
| 5,941,879 A | 8/1999 | Walulik et al. | |
| 6,235,029 B1 | 5/2001 | Faccioli et al. | |
| 7,261,713 B2 * | 8/2007 | Langmaid | A61B 17/6416 606/59 |
| 7,507,240 B2 | 3/2009 | Olsen | |
| 8,182,483 B2 | 5/2012 | Bagnasco et al. | |
| 2004/0097944 A1 | 5/2004 | Koman et al. | |
| 2006/0229602 A1 | 10/2006 | Olsen | |
| 2006/0229605 A1 | 10/2006 | Olsen | |

OTHER PUBLICATIONS

International Preliminary Report on Patentability, PCT/IB2009/006735, dated Dec. 28, 2010, 5 pages.

* cited by examiner

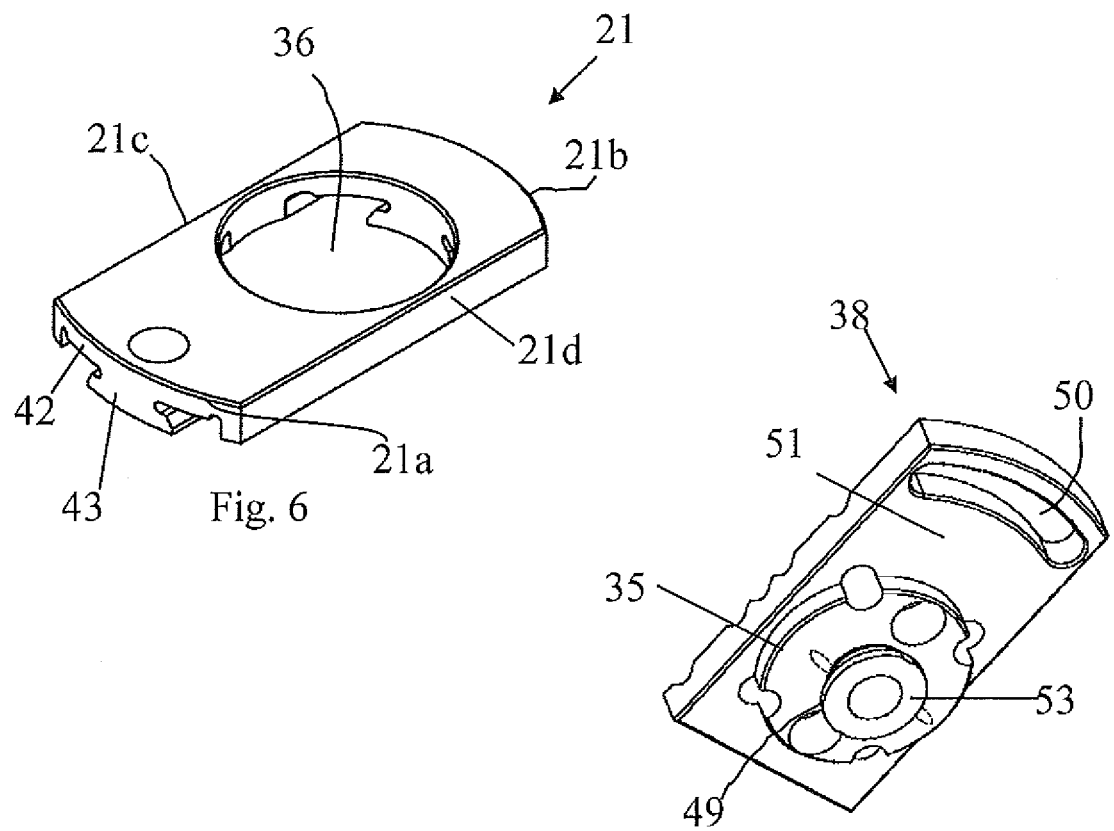
Fig. 6
Fig. 7
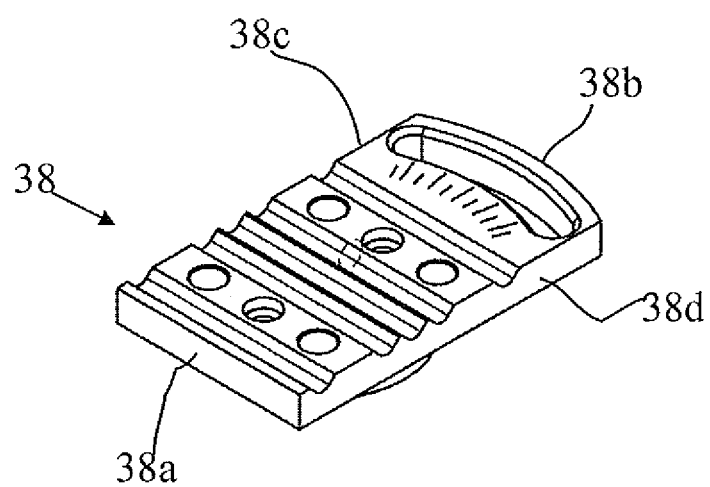
Fig. 8

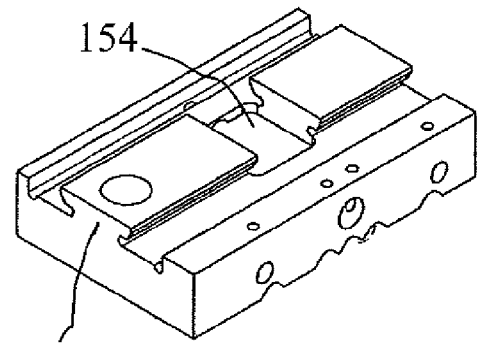
Fig. 18
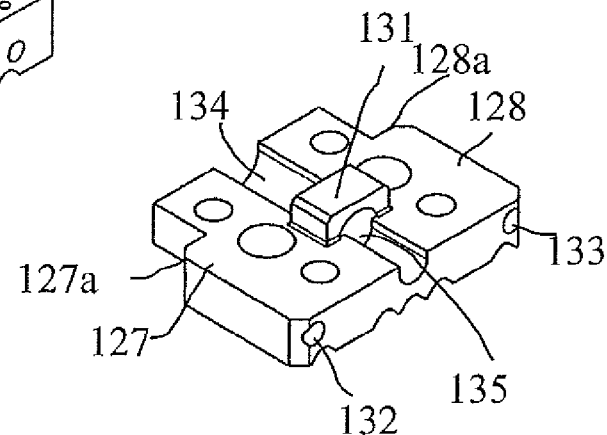
Fig. 19
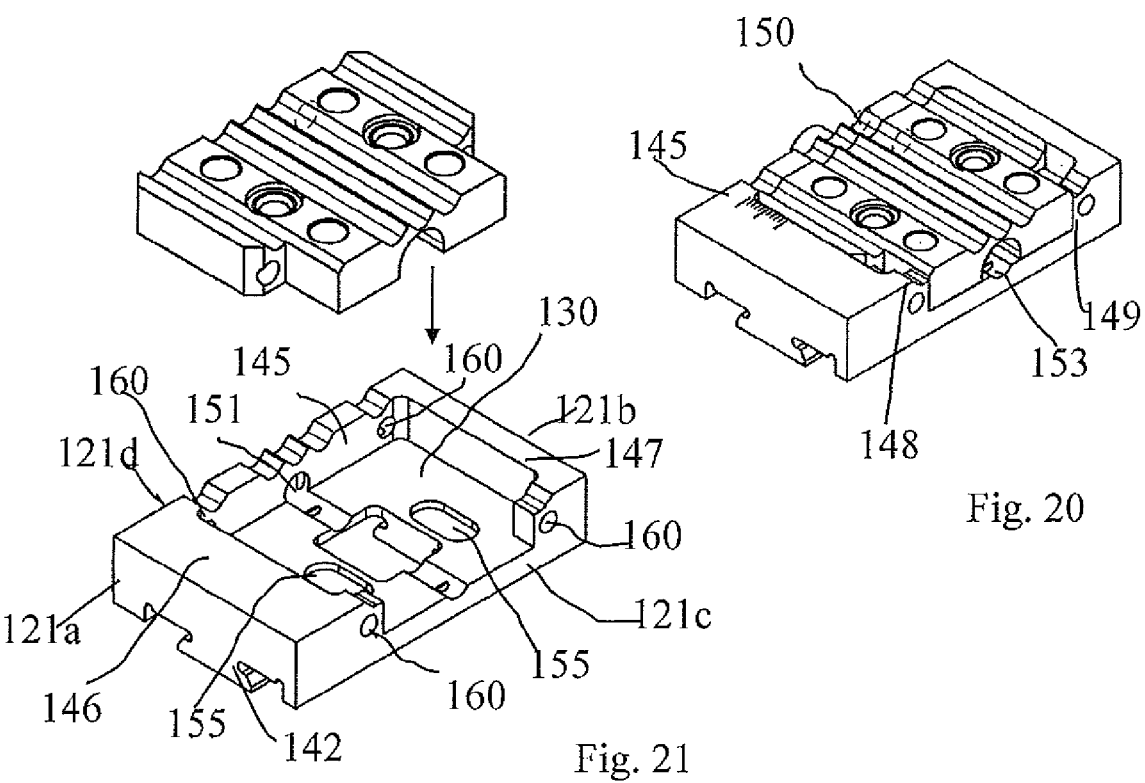
Fig. 20
Fig. 21

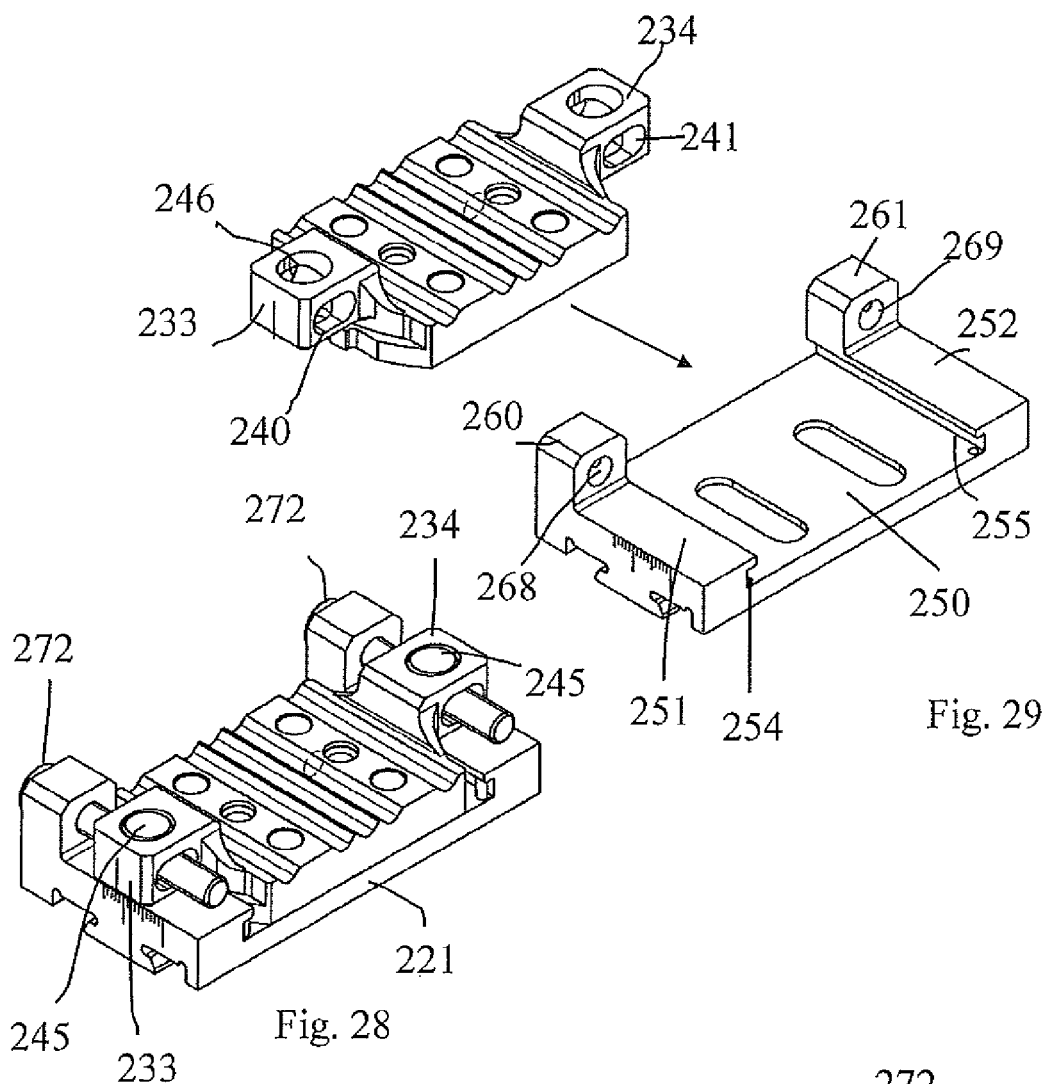
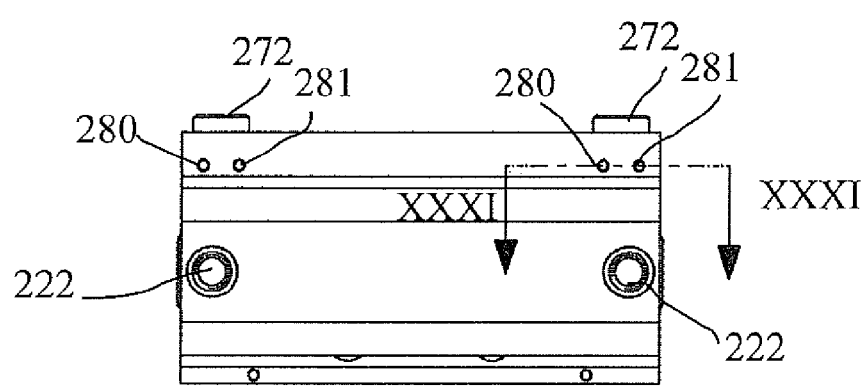

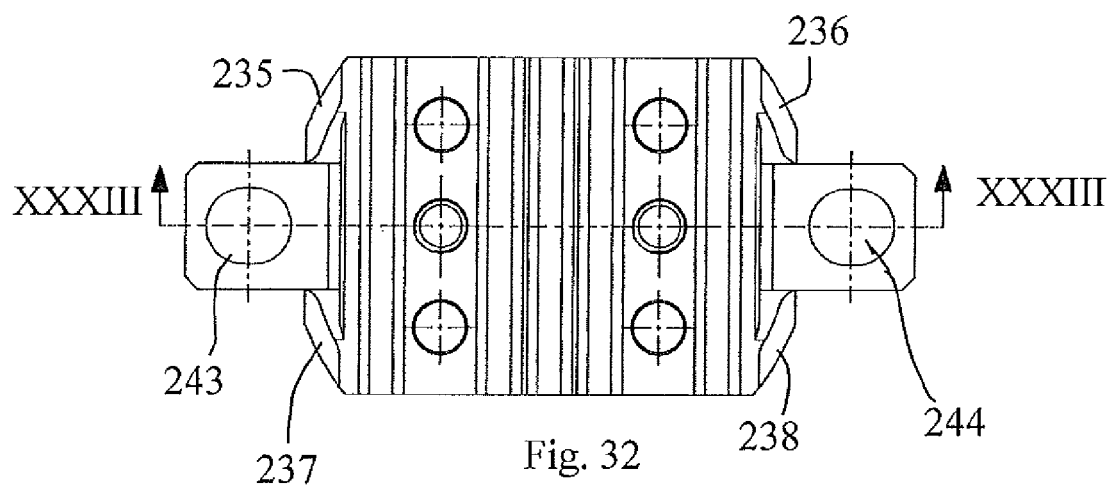
Fig. 32
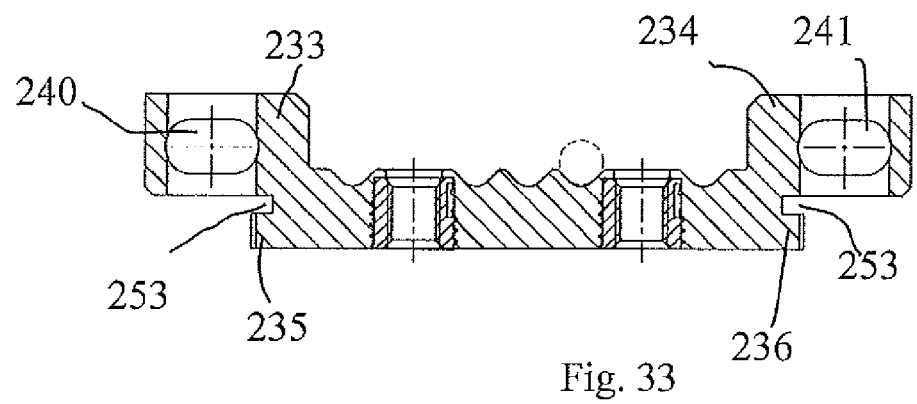
Fig. 33
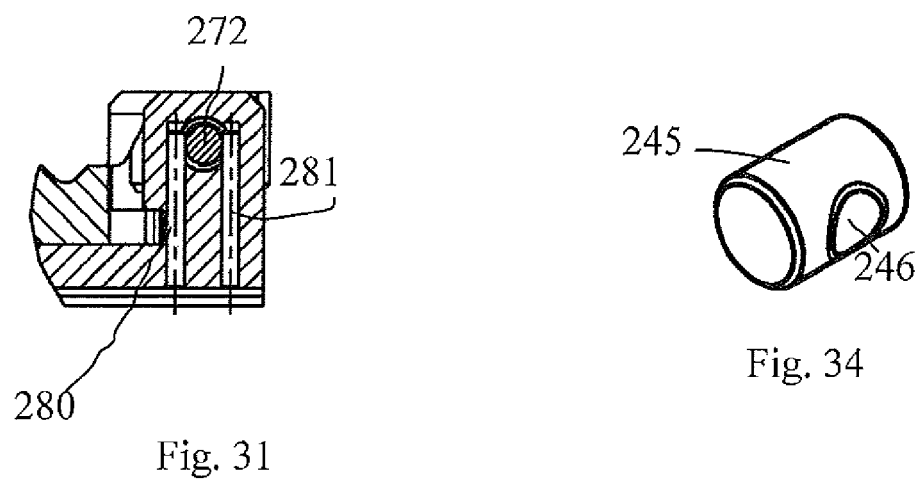
Fig. 31
Fig. 34

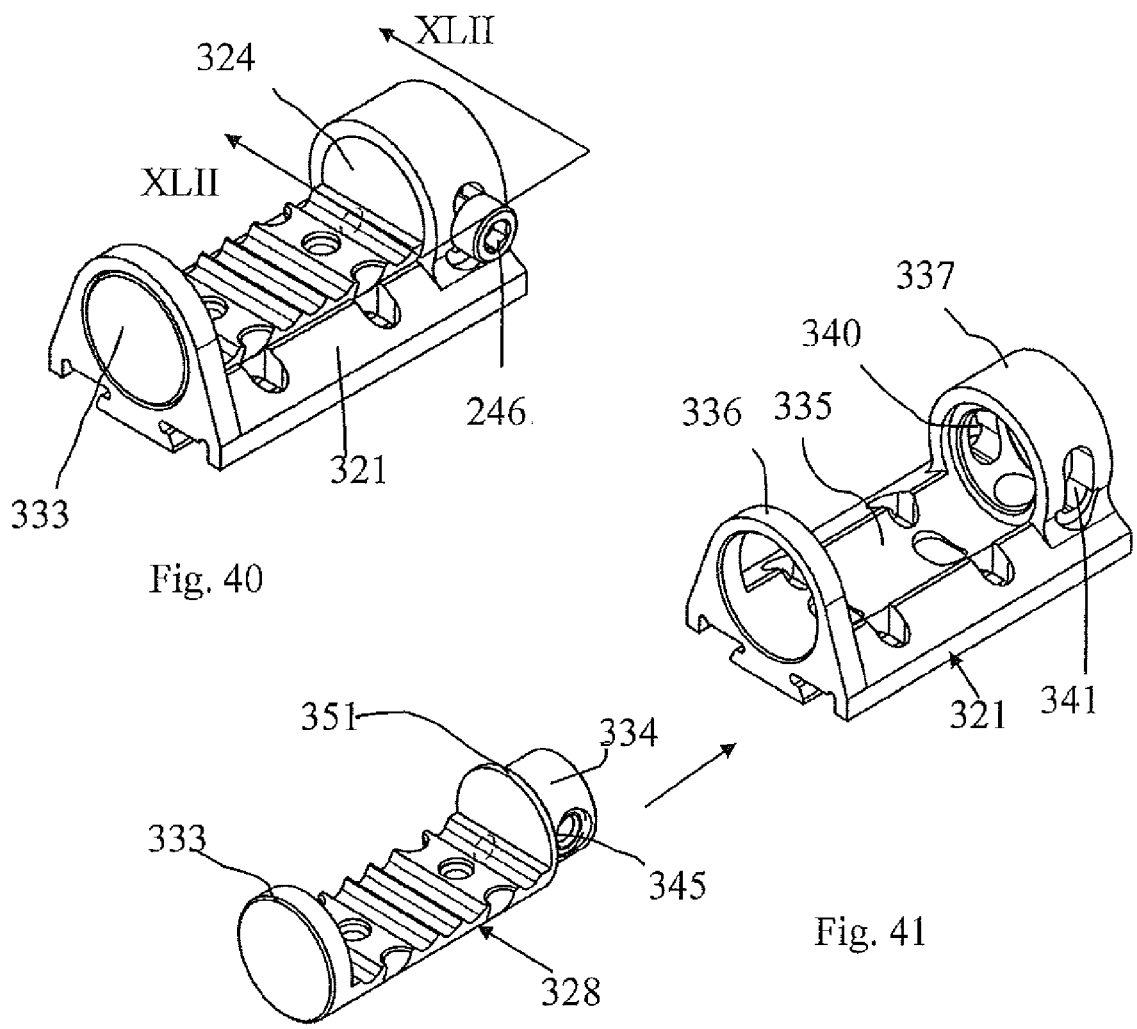

ORTHOPAEDIC DEVICE FOR CORRECTING DEFORMITIES OF LONG BONES

CROSS-REFERENCE TO RELATED APPLICATIONS

The present application is a continuation application from and claims priority to U.S. application Ser. No. 13/063,510 filed Mar. 11, 2011 which is a 371(c) national stage entry of PCT/IB09/06735 filed Sep. 14, 2009. These applications are incorporated herein by reference in their entirety for all purposes.

FIELD OF APPLICATION

The present invention refers to an orthopaedic device for correcting deformities of long bones.

The device is of the type comprising a longitudinal bar extending along a given axis, able to be positioned outside of the bone, and at least a first clamp for a first group of osseous screws, and a second clamp for a second group of osseous screws, respectively, in which said clamps are removably mounted on said longitudinal bar and in which the first of said clamps is placed onboard a support base, in turn mounted on said longitudinal bar and it is angularly movable by means of a rotary coupling around a given rotation axis in relation to the longitudinal bar.

PRIOR ART

In order to correct some deformities of a long bone it is known to use the technique of subjecting the bone to osteotomy forming two or more pieces, and positioning the two pieces in contact with one another in a correct position to allow the formation of fibrocartilage callus.

It is also known that, in the case of deformities that consist of a curvature that does not correspond to the natural curvature of the long bone, so-called angular deformities, it is necessary, in addition to placing the pieces in contact with one another, to adjust the mutual angular position of the two pieces, to reset the correct natural shape of the bone.

In general, it is known that there is a need to have an orthopaedic device, in which it is possible to adjust the mutual angular position of the osseous screws to consequently adjust the mutual angular position of the pieces based on the shape and curvature of the deformed bone that must be corrected.

In order to keep the two pieces in the correct position, it is known to use an orthopaedic device of the aforementioned type outside of the bone, in other words comprising a longitudinal bar positioned externally on one side of the bone, and on which clamps are slidably mounted that hold respective groups of osseous screws.

The osseous screws are locked in the bone pieces to keep them in contact with one another.

Even more specifically, there is an orthopaedic device that has been devised, which is described in patent application VR97A000013 to the Applicant, which comprises angular adjustment means of the two clamps with respect to one another. In particular, one of the two clamps is mounted onboard a support base, which is rotatably mounted, by means of a rotary coupling, about a substantially longitudinal axis, parallel to the longitudinal axis of the bar. Even more specifically, the support base is mounted on an intermediate body, which is hinged by means of a substantially transversal axis to a bracket, in turn rotatably mounted about a longitudinal axis on the longitudinal bar.

Stops screws are foreseen to block the support base about the longitudinal axes and the bracket in relation to the intermediate body and the longitudinal bar, respectively.

An angular displacement of the clamp occurs gradually through a screw having an end hinged to the intermediate body, the opposite end provided with an encased hexagon, and the central portion engaged in a nutplate integral with the bracket.

The known orthopaedic device, whilst advantageous from various points of view, and substantially meeting the purpose, does however involve drawbacks that have not yet been overcome.

The main drawback of the known orthopaedic device is the fact that the first angularly moveable clamp can only be arranged at an end of the guiding bar, thus offering a limited possibility of use along the entire extension of the longitudinal bar.

A further drawback of the known orthopaedic device is the fact that the angularly moveable clamp gives the orthopaedic device large overall bulk, to the detriment of its practicality and comfort of use by a patient.

The technical problem forming the basis of the present invention is, therefore, to devise an orthopaedic device having a structure such as to overcome the aforementioned drawbacks in relation to the prior art.

SUMMARY OF THE INVENTION

The aforementioned technical problem is solved by an orthopaedic device of the aforementioned type, in which the rotary coupling comprises a male element associated with the first clamp and at least partially having a cylindrical surface, and which is loosely received in a corresponding female element, which is the seat for the male element, associated with the support base.

Basically, the idea forming the basis of the present invention is to make a rotary coupling of a cylindrical male element in a female seat directly between the clamp and the support base. This configuration allows the overall bulk of the orthopaedic device to be kept low, as well as making it possible to position the clamp in any position along the longitudinal bar.

A further advantage of the invention is also the fact that the rotary coupling between the at least partially cylindrical surface of the male element and the corresponding female seat, where such an element is loosely received, makes it possible to obtain a wide angular displacement excursion, and at the same time allowing the clamp and the relative base to be positioned in any position along the longitudinal bar.

Moreover, such a coupling makes it possible to have an orthopaedic device that overall is compact and of minimal bulk.

A further advantage of the rotary coupling with cylindrical male element and relative female seat directly between the first clamp and the support base is the possibility of developing a wide assortment of interchangeable embodiments, with different rotary couplings, depending on requirements and the bone deformities to be corrected.

In particular, in a first embodiment, the orthopaedic device is configured so that the rotation axis is perpendicular to a plane that passes through the longitudinal bar and the osseous screws, to allow an adjustment of the angular position on said plane of the first group of osseous screws going towards or away from the bone, in relation to the other group of osseous screws.

In such a first embodiment, preferably, the first clamp comprises a cylindrical projection with axis coinciding with the rotation axis, which therefore acts as the male element, which is received in a circular hole that is formed in the support base.

Preferably, the support base and the first clamp have a substantially rectangular shape with respective long sides and short sides, and the cylindrical projection and the circular hole extend with maximum possible diameter between the two opposite long sides of the lower jaw, and of the support base, so as to ensure maximum stability in rotation.

In order to guide the angular displacement, in this first embodiment, a guiding slot is foreseen that is shaped like an arc of circle with its centre on the rotation axis, in which said slot is formed in the first clamp, and in which a clamping screw is inserted into said slot screwed into the support base.

Preferably, in order to carry out the angular displacement a compressor/distractor is foreseen comprising a driving screw, and which is removably connected to the first clamp and the second clamp, and more specifically the compressor/distractor is connected to the first clamp by means of a lever connection element having an arm that extends laterally in relation to the rotation axis. This lever connection element allows the force needed from a user to carry out the angular displacement to be reduced.

In this first embodiment, the second clamp comprises two jaws that are mounted directly onboard the longitudinal bar.

Unlike this first embodiment, in a second embodiment the second clamp can translate in relation to the longitudinal bar transversally in relation to the axis of the longitudinal bar, with a linear reciprocating movement towards and away from the bone. This linear movement allows a displacement of the bone after the angular displacement to be compensated, if necessary.

Preferably, in this second embodiment, the second clamp is mounted onboard a carriage, and it can translate in relation to the carriage with said linear movement, by means of a driving screw, which rotates but does not translate, and which has its shank inserted and held axially in a hole of the carriage, and connected through screwing to the second clamp.

In a third embodiment of the orthopaedic device according to the present invention, the first clamp is both angularly movable in relation to the support base with angular displacement about an axis orthogonal to the plane that passes through the osseous screws, and linearly translatable in relation to the support base with linear reciprocating movement parallel to said plane, in a transversal direction, when approaching and moving away from the bone respectively.

Basically, in this third embodiment, by means of the same first clamp an angular displacement and a linear translation are carried out, to make the aforementioned compensation of the displacement of the bone due to the angular displacement, if necessary. Consequently, in this third embodiment the second clamp is not of the translatable type, but comprises, like the first embodiment, two jaws that are mounted directly onboard the longitudinal bar.

In this third embodiment, in order to make both the angular and linear displacements, the orthopaedic device comprises two driving screws, which rotate but do not translate, and that are inserted and held axially at the sides of the seat for the male element in corresponding holes of the support base, and screwed into the first clamp at the sides of the male element, in which said driving screws are actuated together in rotation with opposite directions of rotation for the angular displacement, and actuated together in rotation with the same direction of rotation to carry out the linear reciprocating movement.

Preferably, in this third embodiment, the first clamp comprises an upper jaw and a lower jaw, closed together by means of two clamping screws, in which the lower jaw has a substantially U-shaped profile, and comprises, in a single body, a central block with a substantially rectangular shape, two lateral appendices, which project laterally in an overhanging manner in relation to the central body and on the bottom of the central block, at the four corners thereof, respective flaps having a cylindrical profile, in which such flaps constitute a male element for the angular displacement of the first clamp.

The driving screws are screwed into each of the lateral appendices.

The support base of this third embodiment comprises a substantially plate-like body in which a recess is formed having a substantially rectangular shape, which forms lateral edges at the sides, and in which each lateral edge on the side facing towards the recess has a segment having an inverted L-shaped profile that defines two linear sliding guides, said recess and the two sliding guides defined by it act as a seat for the aforementioned four flaps, thus for the male element.

A corresponding driving screw is inserted at each lateral edge, and it is held there by means of elastic pins received in a gorge of the driving screw formed between the head and the shank.

In a fourth embodiment, the first clamp is angularly movable in relation to the longitudinal bar about an axis, parallel to the axis of the longitudinal bar to allow an angular displacement of swinging type of the osseous screws. The orthopaedic device in accordance with this embodiment is adapted to be placed at the side of a long bone having a natural curvature, like for example a femur. The first clamp is placed at such a curvature and is inclined about the rotation axis so as to be able to reach the bone with the osseous screws. The first clamp is locked in the desired angular position by means of a locking screw inserted in the support base, and screwed into the first clamp.

In this fourth embodiment, the first clamp comprises an upper jaw, and a lower jaw, closed together by means of locking screws, in which the lower jaw is substantially C-shaped, and comprises a central plate-like body, having a substantially rectangular shape, and, at the sides, a first cylindrical body and a second cylindrical body both having an axis coinciding with the rotation axis, in which said cylindrical bodies constitute a male element.

The support base is substantially C-shaped and comprises a substantially plate-like rectangular central body on which the plate-like body of the first clamp is placed, having, at the relative sides, a first annular body and a second annular body, both having an axis coinciding with the rotation axis, in which cylindrical holes are formed, for loosely receiving the first and the second cylindrical body. Such annular bodies thus act as seats for the male element/cylindrical bodies.

The locking screw is preferably inserted in a slot made in the second annular body of the support base, and screwed into the second cylindrical body of the first clamp.

Preferably, in this fourth embodiment, the second clamp is not of the translating type, but comprises, like in the first embodiment, two jaws that are mounted directly onboard the longitudinal bar.

Further characteristics and advantages of the orthopaedic device according to the invention shall become clearer from the following description of some example embodiments given for indicating and not limiting purposes with reference to the attached drawings.

BRIEF DESCRIPTION OF THE DRAWINGS

FIG. 6 is an axonometric view from above of a support base of the clamp of FIG. 3;

FIG. 7 is an axonometric view from below of a lower jaw of the clamp of FIG. 2;

FIG. 8 is an axonometric view from above of the jaw of FIG. 7;

FIG. 18 is an axonometric view from below of a carriage of the clamp of FIG. 14;

FIG. 19 is an axonometric view from below of a lower jaw of the clamp of FIG. 15;

FIG. 20 is an axonometric view of a detail of the clamp of FIG. 15;

FIG. 21 is an axonometric view with parts detached of the detail of FIG. 20;

FIG. 25 is an axonometric view of a clamp of the orthopaedic device of FIGS. 24 and 24a;

FIG. 28 is an axonometric view of a detail of the clamp of FIG. 25;

FIG. 29 is an axonometric view with parts detached of the detail of FIG. 20;

FIG. 30 is a plan view from below of the clamp of FIG. 25;

FIG. 31 is a section view along the line XXXI-XXXI of FIG. 30;

FIG. 32 is a view from above of the lower jaw of the clamp of FIG. 25;

FIG. 33 is a section view along the line XXXIII-XXXIII of FIG. 32;

FIG. 34 is an axonometric view of a bolt for the clamp of FIG. 25;

FIG. 40 is an axonometric view of a detail of the clamp of FIG. 37;

FIG. 41 is an axonometric view with parts detached of the detail of FIG. 40;

FIG. 42 is a view from above partially in section along the line XLII-XLII of FIG. 40.

DETAILED DESCRIPTION

Figure 1:
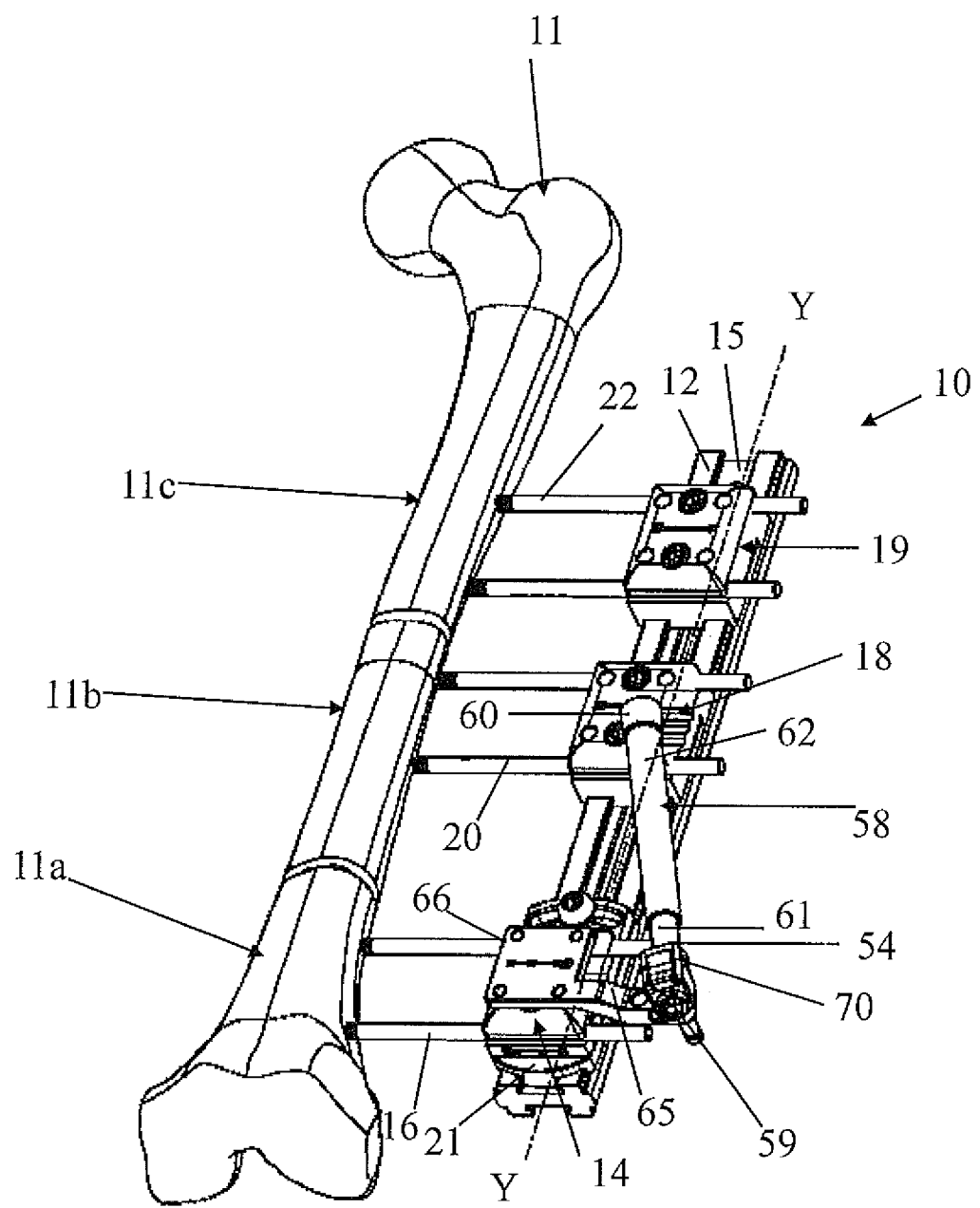
FIG. 1 is an axonometric view of an orthopaedic device according to the invention in accordance with a first embodiment.
Figure 2:
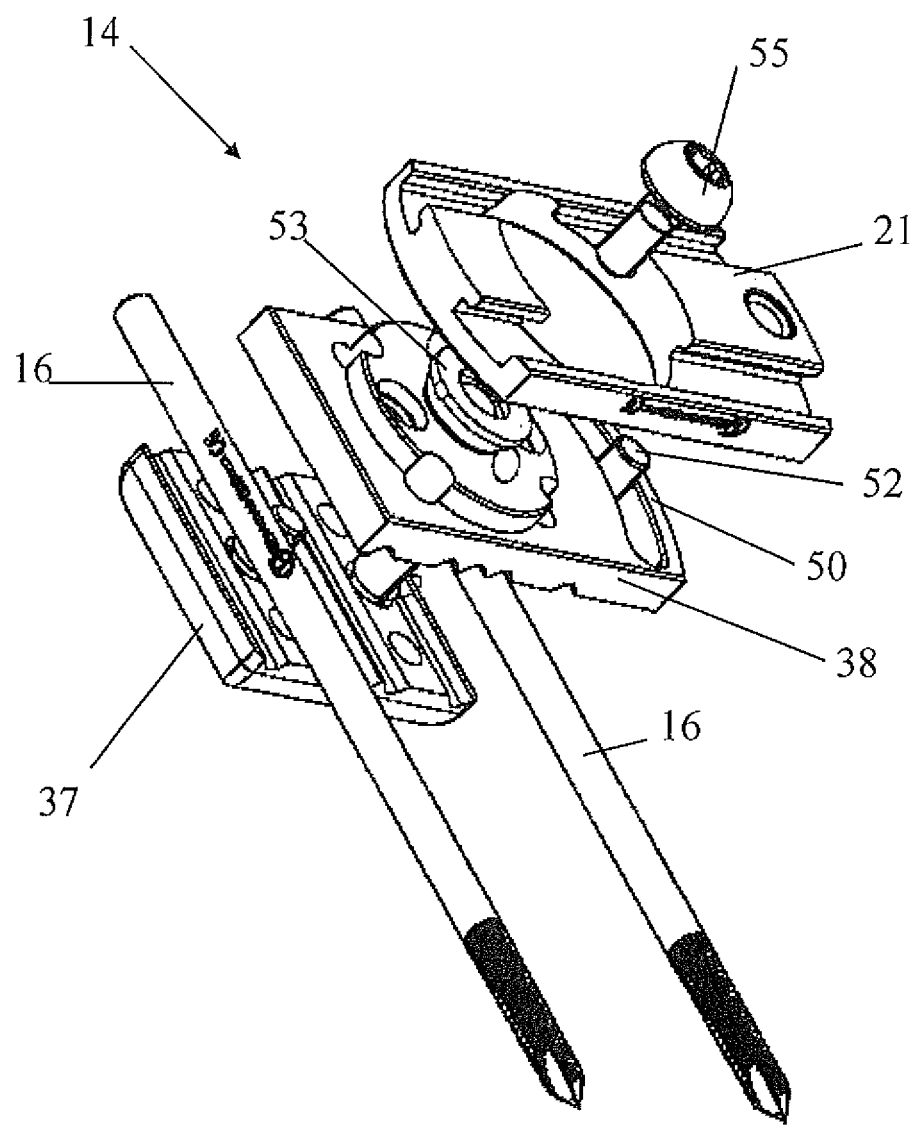
FIG. 2 is a view of a clamp of the orthopaedic device of FIG. 1, with parts detached.
Figure 3:
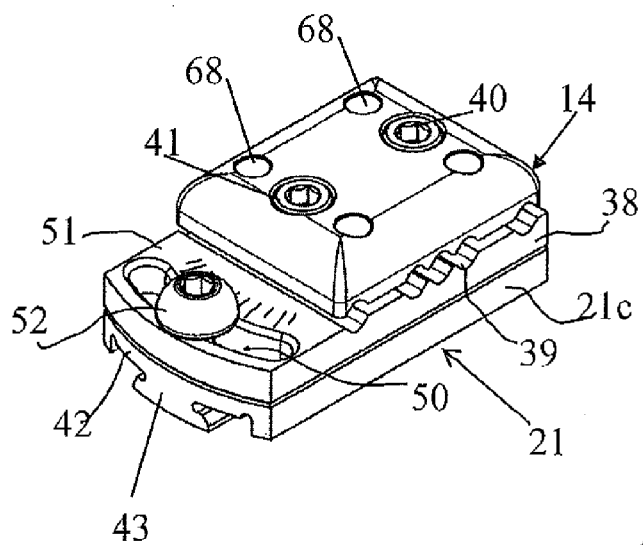
FIG. 3 is an axonometric view of the clamp of FIG. 2.
Figure 4:
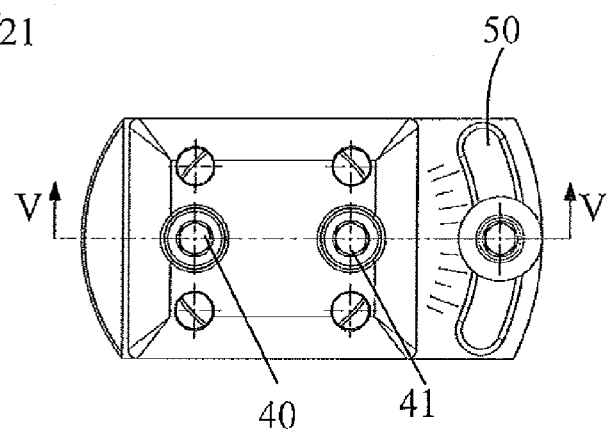
FIG. 4 is a plan view of the clamp of FIG. 3.
Figure 5:
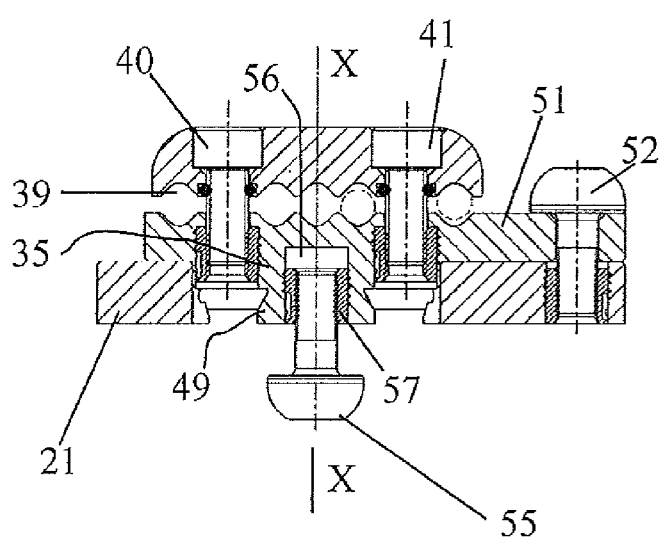
FIG. 5 is a section view along the lines V-V of FIG. 4.
Figure 4A:
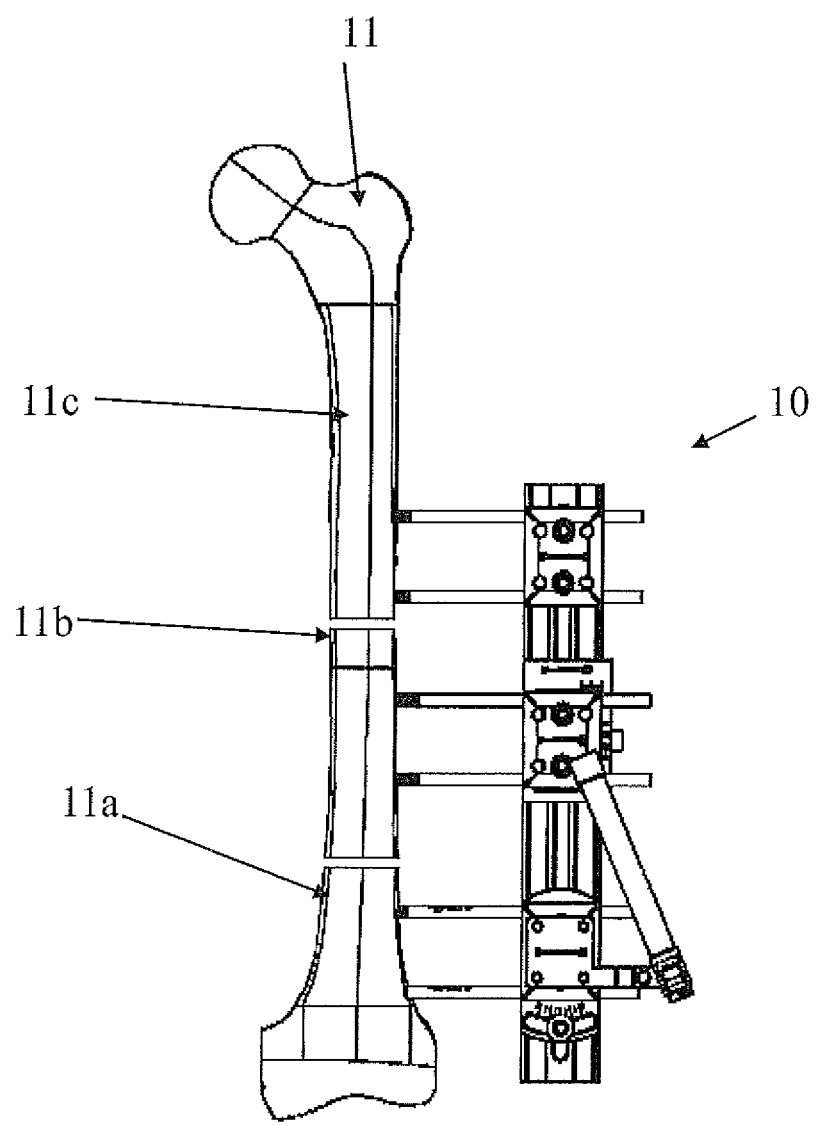
FIG. 4a is a front view of a long bone separated into three pieces with which an orthopaedic device according to the invention is associated with a T-section bar.

With reference to the attached figures, reference numerals 10, 110, 210, 310 indicate different embodiments of an orthopaedic device according to the present invention for correcting deformities of a long bone 11, in the examples a tibia, or a femur. In particular, as highlighted in the relative figures indicated above, in order to allow the correction of the deformity, the bone 11 has been subjected to osteotomy with the formation of two pieces 11a, 11b (FIG. 1) or to bifocal osteotomy with the formation of three pieces 11a, 11b, 11c.

In particular, FIGS. 1 to 13 refer to an orthopaedic device 10 in accordance with a first embodiment.

Such an orthopaedic device 10 comprises a bar 12, which we shall also define hereafter as longitudinal bar and which is made, for example, with synthesis materials like: Orthtek WF®, pultruded with carbon fibre in epoxy resin, or Peek CA30®. The bar 12 can also be made, for example, from aluminium alloy. Such a bar 12 extends along a given axis Y-Y, and is intended to be placed laterally and substantially parallel to the bone 11. The orthopaedic device according to the invention also comprises at least one first clamp 14 for a first group of osseous screws 16 screwed into a first piece 11a of the bone and a second clamp 18 for a second group of osseous screws 20 screwed into a second piece 11b of the bone. These clamps can also be made from Peek CA30® with steel, titanium alloy or aluminium alloy inserts.

In the example of FIG. 1, the orthopaedic device 10 also comprises a third clamp 19 for a third group of osseous screws 22 also intended to be screwed into a third piece 11c of the bone.

All three clamps 14, 18 and 19 are removably mounted on the longitudinal bar 12.

In particular, the second clamp 18 and the third clamp 19 are the same as one another, (FIGS. 9, 10, and 11), and each of them comprises an upper jaw 23 and a lower jaw 24 closed together by means of two clamping screws 25, 26; the clamping screws are preferably made from steel and/or titanium alloy, although other materials may be equally suitable. Each of them comprises transversal grooves defining transversal seats 29 for housing the osseous screws 20, 22.

Elastic rings 33, made from silicon or another material, are foreseen arranged inside suitable gorges in the upper jaw 23 and provided for give friction to the clamping screws 25, 26.

The lower jaw 24 is substantially a fixed jaw if considered in relation to the upper jaw 23 that is removably guided towards and away from such a lower jaw 24. Of course, the lower jaw 24 should not be considered to be fixed in relation to the bar 12 on which, conversely, it is slidably guided like a carriage.

Such a lower jaw 24 has a substantially T-shaped profile with a vertical core 27 in turn having an inverted T-shaped profile slidably inserted in a matching inverted T-shaped groove 15 of the longitudinal bar 12, and locked in a given longitudinal position by means of a locking screw 28.

In particular, the latter is inserted from below in a longitudinal hole of the longitudinal bar 12, and screwed into the lower jaw 24 of the clamp 18, 19.

The lower jaw 24 also has lateral fins provided to prevent the two jaws from opening when they are subjected to bending moment.

Figure 9:
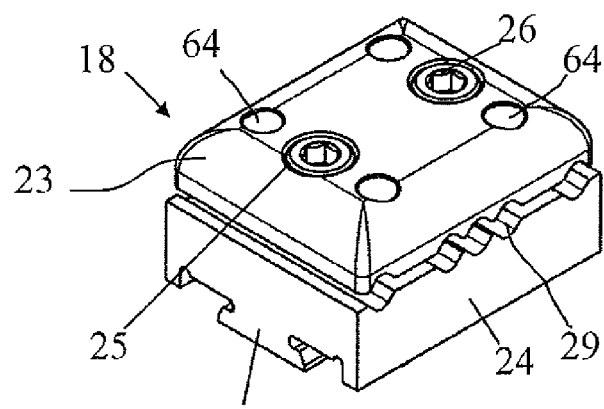
FIG. 9 is an axonometric view of another clamp of the orthopaedic device of FIG. 1.
Figure 10:
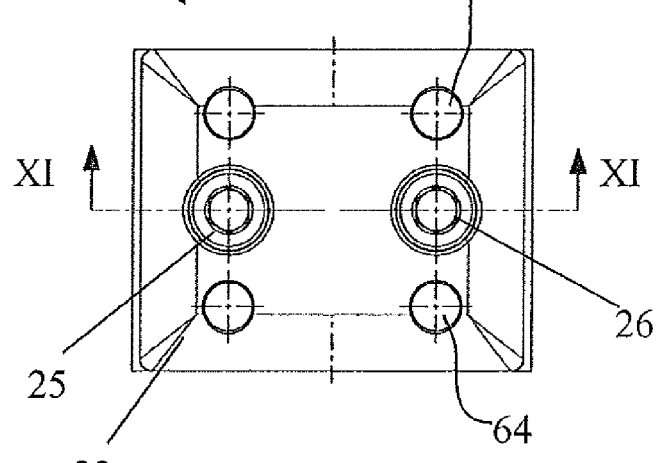
FIG. 10 is a plan view of the clamp of FIG. 9.
Figure 11:
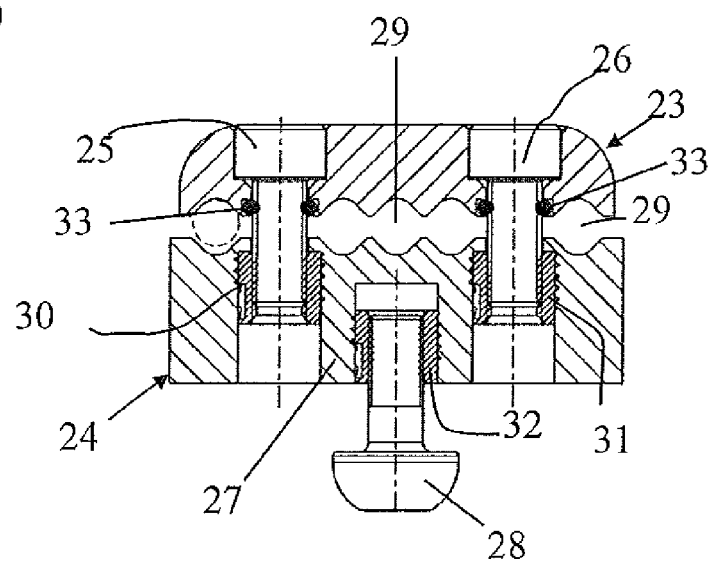
FIG. 11 is a section view along the line XI-XI of FIG. 10.

As illustrated in FIGS. 9, 10, 11, all of the screws 25, 26, 28 are screwed not directly into the body of the clamp, in the example into the body of the lower jaw 24, but into respective hollow inserts 30, 31, 32 preferably made from steel, or else aluminium or titanium alloy, internally threaded, and having a substantially cylindrical shape.

Such inserts 30, 31, 32 are also externally threaded, and in turn locked in the lower jaw 24 by means of screwing.

Figure 12:
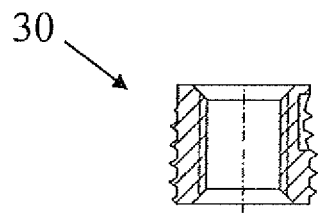
FIG. 12 is an axonometric view of an insert of the orthopaedic device of FIG. 1.

One of such inserts 30 is illustrated in FIG. 12.

In particular, the orthopaedic devices 10, 110, 210, 310 of the embodiments described hereafter are provided with further identical inserts for the locking screws to screw into. For the sake of simplicity and briefness of description, hereafter the description of such inserts will be omitted.

Unlike the two clamps 18 and 19, the first clamp 14 is arranged onboard a support base 21, which is in turn slidably mounted on said longitudinal bar 12.

The clamp 14 is also angularly movable in relation to the support base 21 by means of rotary coupling of a male element in a female element, and consequently in relation to the longitudinal bar 12 about a given rotation axis, in the example an axis X-X (FIG. 2) perpendicular to a plane that passes through all of the osseous screws 16, 20, 22, to allow adjustment of the angular position on said plane of the osseous screws 16 in relation to the other osseous screws 20, and 22, and thus of the pieces 11a, 11b and 11c of bone connected to them.

In particular, in order to allow the angular displacement, the orthopaedic device 10 comprises a cylindrical projection 35 (FIGS. 5 and 7), which constitutes the male element, associated with the clamp 14, and loosely received in a circular hole 36 (FIG. 6), which acts as a female seat for the male element, which is associated with the support base 21.

In particular, in this embodiment, the first clamp 14 comprises an upper jaw 37 (not to be confused with the upper jaw 23 of the second and third clamp 18, 19), constituting a removable cover of the clamp 14, and a lower jaw 38 (not to be confused with the lower jaw indicated with 24) constituting the fixed base of the clamp 14, and both of the jaws 37 and 38 are substantially rectangular in shape.

In particular, the lower jaw 38 is larger in size than the upper jaw 37, with short sides 38a, 38b, and long sides 38c, 38d, and it comprises, at a short side 38b, a lateral extension 51 having a curved profile.

Even more specifically, the lower jaw 38 comprises the aforementioned cylindrical projection 35. Such a cylindrical projection 35 projects from a side of the lower jaw 38 opposite to the one facing towards the upper jaw 37.

Like for the clamps 18 and 19, the first clamp 14 is also provided with transversal seats 39 to receive the groups of screws 16, and with two locking screws 40, 41 (FIG. 5, not to be confused with the clamping screws 25, 26 of the other clamps 18 and 19) to close together the upper jaw 37 and the lower jaw 38.

The support base 21 (FIG. 6) comprises a plate-like body having a substantially rectangular shape with curved short sides 21a, 21b and straight long sides 21c, 21d, and a substantially T-shaped transversal profile with an upper wing 42 constituting a support for the clamp 14 and lower vertical core 43, having the same shape as the vertical core 27 of the clamps 18 and 19, and thus also having an inverted T-shaped profile, which is slidingly inserted in the longitudinal groove 15 of the longitudinal bar 12.

As stated above, in the support base 21 the through hole 36 is made, constituting the aforementioned seat for the male element, in which the aforementioned cylindrical projection 35 is loosely received.

It should also be observed that the cylindrical projection 35 and the circular hole 36 occupy a substantial part, and in particular they extend with maximum possible diameter between the two opposite long sides 38c, 38d, 21c, 21d of the lower jaw 38, and of the support base 21 respectively, in the example with a diameter of 36 mm.

With such a configuration, the first clamp 14 is angularly movable about the axis X-X, by means of rotation of the cylindrical projection 35 in the corresponding circular hole 36 of the support base 21.

In order to guide the angular displacement of the clamp 14 about the axis X-X, the orthopaedic device 10 comprises a guiding slot 50 having an arc of circle shape with centre on the axis X-X, made on the lateral extension 51 of the lower jaw 38. The arched extension of the guiding slot 50 is sufficiently large, in the example the slot subtends an angle to the centre of about 50°, in particular an angular displacement up to 25° going towards the bone 11, and an angular displacement up to −25° going away from the bone 11.

In order to block the clamp 14 in whatever angular position in relation to the support base 21, a clamping screw 52 is foreseen inserted from above into the guiding slot 50, and screwed into an internally threaded insert inserted into the support base 21.

As can be observed from the drawings, and in accordance with another aspect of the orthopaedic device 10, the lower jaw 38 of the clamp 14 is also fixed directly to the longitudinal bar 12.

Basically, the clamp 14 is also connected to the longitudinal bar 12. In particular, the lower jaw 38 of the clamp 14 comprises a coupling element 53 projecting coaxially from the cylindrical projection 35 of a smaller size in relation to the projection 35, and having a substantially T-shaped profile. In practice, such a coupling element 53 is inserted laterally by sliding in the T-shaped groove 15 of the longitudinal bar 12. Thanks to the T-shaped countershaping, the coupling element 53 constrains the first clamp 14 in the groove 15 of the longitudinal bar 12, and the constrainment can only be removed by withdrawing from the groove 15 itself.

Even more specifically, the coupling element 53 has a cylinder shape at an end segment 49, to promote the angular displacement about the axis X-X in the groove 15.

In order to stably lock the clamp 14 in a predetermined axial position on the longitudinal bar 12, a clamping screw 55 is foreseen, which is inserted into the aforementioned longitudinal through hole 13 of the longitudinal bar 12 and into the circular hole 36 of the support base 21, and is screwed into a hole 56 equipped with a cylindrical insert 57 formed in the coupling element 53. In order to lock the angle between support base 21 of the clamp 14 and longitudinal bar 12 it is thus necessary to clamp the screw identified with numeral 52.

In order to carry out the angular displacement of the osseous screws 16 carried by the first clamp 14 in relation to the support base 21, the orthopaedic device 10 comprises a compressor/distractor 58 (FIG. 1) that can be removably coupled between the first clamp 14 and the second clamp 18.

The compressor/distractor 58 comprises a driving screw 54 having a threaded shank 61 and, at both ends, a first portion off head 59, facing towards the first clamp 14, and a second portion of head 60, facing towards the second clamp 18, both provided with an encased hexagon. By using a tool on such encased hexagons, it is possible to manoeuvre the screw 54 in relation to a first internally threaded sleeve 62 in which it is engaged.

Figure 13:
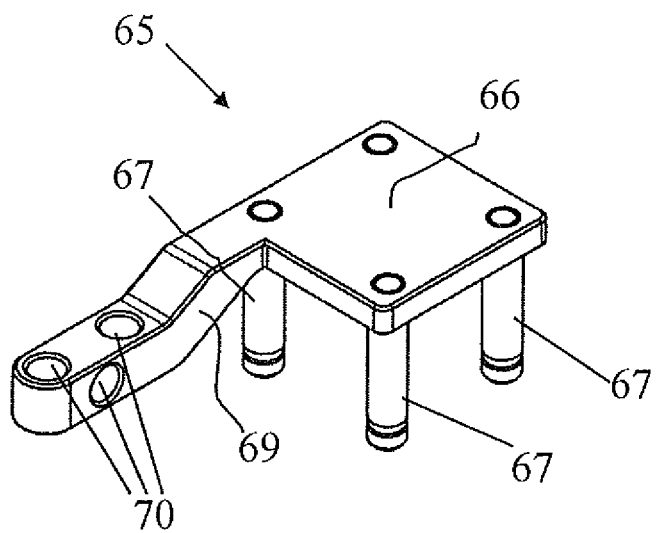
FIG. 13 is an axonometric view of a connection element of the orthopaedic device of FIG. 1.

In particular, the threaded shank 61 of the screw 54 is connected to the first clamp 14 through a connection element 65 that can be made from steel, aluminium alloy or plastic material like Nylon® and silicon, illustrated in FIG. 13, whereas it is connected to the second clamp 18 through the first sleeve 62 provided with internal threading, in which the shank 61 is screwed, in which such a sleeve 62 is provided with an engagement pin inserted into a matching hole 64 formed on the upper jaw 23 of the second clamp 18.

In particular, the connection element 65 comprises a substantially flat plate-like body 66 provided on the lower side with four engagement pins 67 which are pressure-inserted in corresponding engaging holes 68 formed on the upper and lower jaws 37, 38 of the clamp 14, and an arm 69 provided at the free end with at least one eye 70 to which the threaded shank 61 of the screw 54 is loosely connected. In particular, the eye 70 can be axially held between the first head 59 of the screw 54 and an internally threaded ring screwed onto the shank 61 of the screw.

In order to obtain the correction with bone transportation by means of the orthopaedic device 10, the following is carried out.

After having subjected the bone to two osteotomies, the first two pieces of bone are kept in contact with one another in a correct mutual position by means of the orthopaedic device 10, whereas between the second and the third piece there is a space. In particular, initially, the second clamp 18, and the third clamp 19 are slidingly inserted in the groove of the longitudinal bar 12 and fixed there in a predetermined position by means of the clamping screw 28. Once the callus has been generated, by means of the compressor/distractor 58 the clamp 18 is pulled to make the contact between second 11b and third 11c piece. The clamp 14 is slidingly inserted in the groove of the longitudinal bar 12 together with the support base 21. In particular, the cylindrical projection 35 of the lower jaw of the clamp 14 is inserted in the circular hole 36 of the support base 21, and the coupling element 53 is inserted together with the vertical core 43 of the support base 21 in the groove of the longitudinal bar 12.

The clamp 14 is locked to the support base 21 by means of the screw 52, and together with the support base 21 locked to the longitudinal bar 12 through the screw 55.

Between the lower jaws 24, 38 and upper jaws 23, 37 of all three clamps 14, 18, 19 are inserted, and held there through the osseous screws 16, 20, 22 which are screwed into the pieces.

The mutual position of the first clamp 14, of the second clamp 18, and of the third clamp 19 on the longitudinal bar is selected so as to bring together the two pieces until they are in contact and to allow the formation of fibrocartilage callus.

Thereafter, to adjust the angular position of the two pieces by a given angle, the compressor/distractor 58 is mounted by means of insertion of the engaging pins 67 of the flat button 66, and of the engaging pin of the sleeve 62 on the second clamp 18.

The clamping screws 52 and 55 are initially loosened to allow the angular displacement of the clamp 14.

Consequently, by screwing the screw 54 of the compressor 58 in a certain direction of rotation at the first end 59, or at the second end 60, an angular displacement around the axis X-X of the clamp 14 is obtained in relation to the support base 21 towards or away from the bone, respectively. In particular, by screwing the compressor 58 to the first end 59 in one direction of rotation, a positive angular displacement by up to +25° of the clamp 14 is obtained, whereas by screwing at the second end 60 a negative angular displacement by up to −25° of the clamp 14 is obtained.

Once a correct angular position is reached, the first clamp 14 is locked to the longitudinal bar 12 by means of definitive clamping of the screw 55 and to the support base 21 by means of definitive clamping of the screw 52.

A first advantage of the orthopaedic device in accordance with this embodiment is the fact that, thanks to the coupling of the cylindrical surface of the clamp in the circular hole of the support base, it is possible to obtain an adjustment of the angular position with a relatively small overall bulk of the clamp.

Moreover, the rotary coupling of the cylindrical surface in the circular hole allows a wide excursion of angular displacement to be obtained, up to 50°.

A further advantage is given by the large diameter of the cylindrical projection and of the circular hole. Indeed, thanks to such a configuration there is a large contact surface between the male element and the corresponding seat, which ensures high stability of the device during rotation.

A further advantageous aspect is that the angular displacement of the clamp in relation to the support base can be obtained without the need to remove the clamping between the two jaws of the clamp. Basically, the osseous screws can be held between the two jaws during the angular displacement, thus giving the benefit of unusual simplicity of use of the device by a user.

A further advantage is offered by the stable connection between the coupling element of the clamp 14 and the longitudinal bar 12. Indeed, there is the advantage that when the clamping screws 55 and 52 are loosened to allow the angular displacement, or else when there is an accidental loosening or loss of the clamping screw 55, thanks to the stable connection of the coupling element 53 there is not the risk of the clamp 14 accidentally coming out or being lost.

A further advantage is offered by the lateral arm of the connection element. Such an arm allows the compressor to be arranged on a plane that is displaced in relation to the rotation axis, thus reducing the force necessary to obtain the angular displacement of the clamp while the adjustment screw is being screwed in.

Advantageously, the rotation system, guided by a cylindrical guide that is large in size thus giving precision in rotation and a distribution of the stresses over a large area reducing the risk of seizing.

Moreover, the angular correction force is applied through a connection in four symmetrical points in relation to the centre of rotation, generating a correct distribution of the load. The force is also applied onto a high lever arm reducing the force applied for the same resisting moment.

Figure 14:
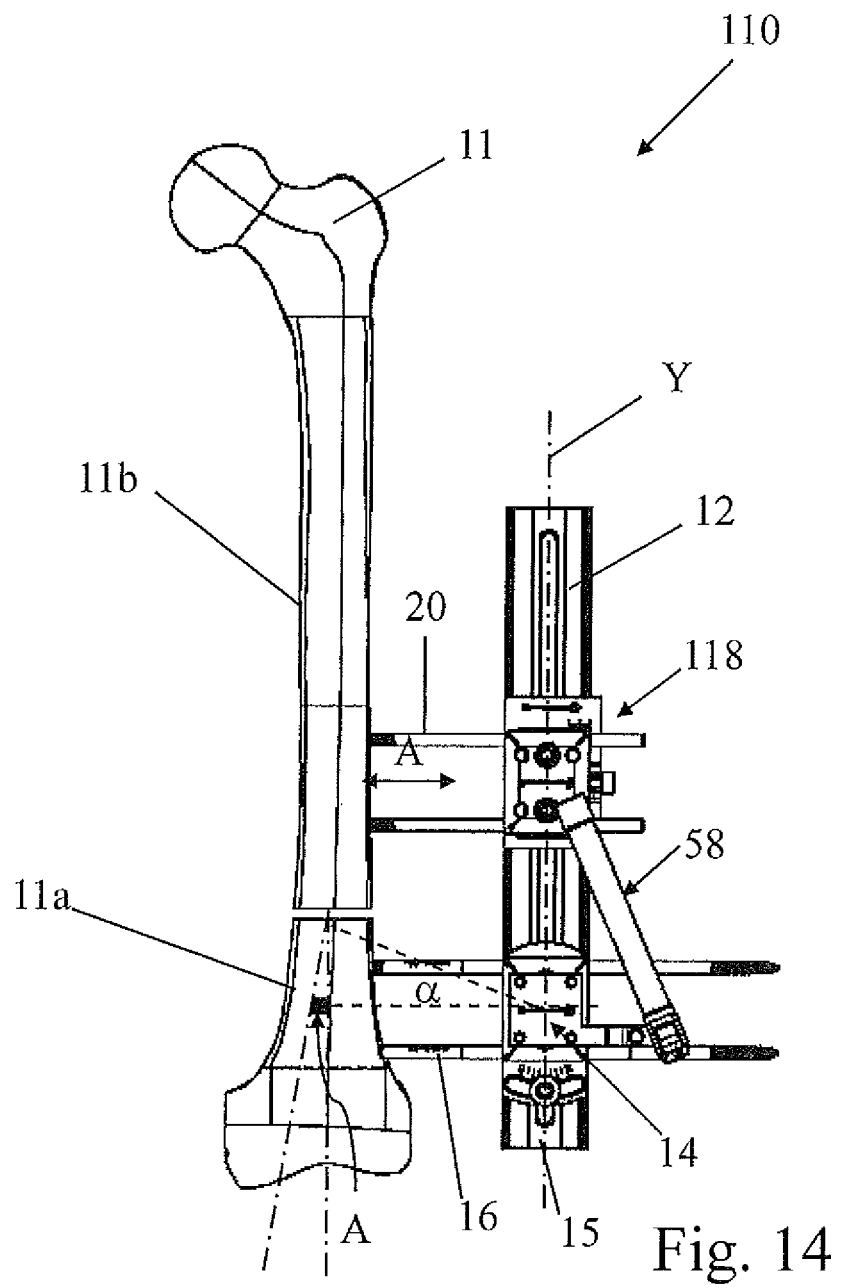
FIG. 14 is a front view of an orthopaedic device according to the invention in accordance with a second embodiment.
Figure 14A:
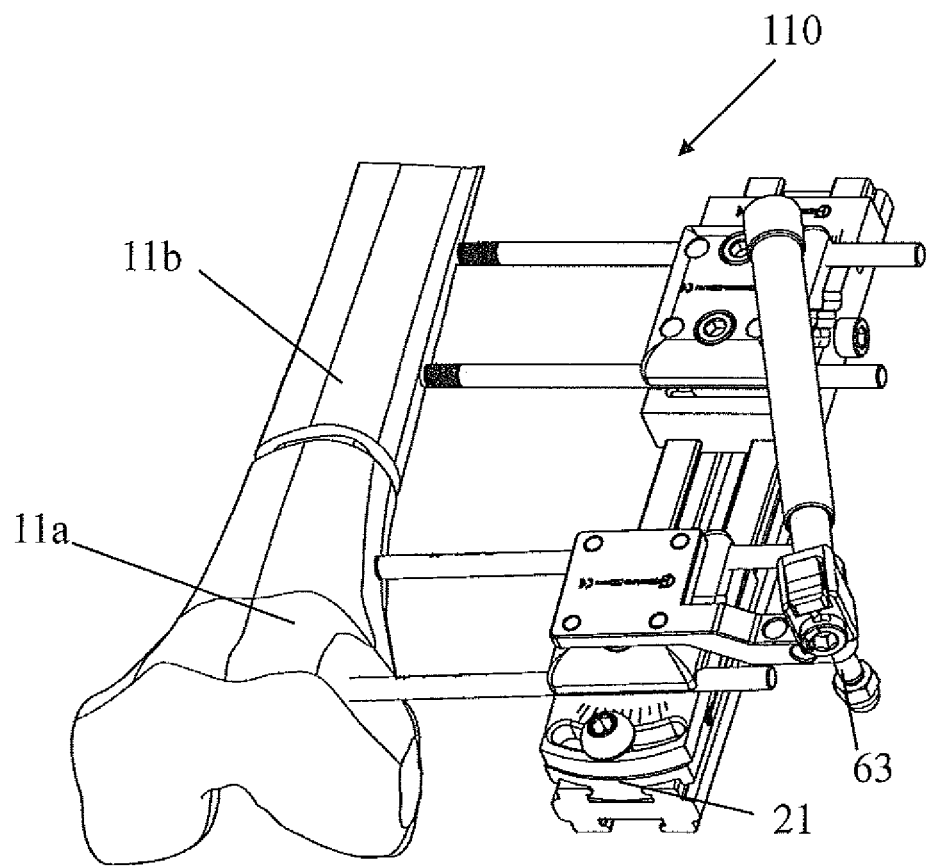
FIG. 14a is an axonometric view of an orthopaedic device according to the invention in accordance with a second embodiment.
Figure 15:
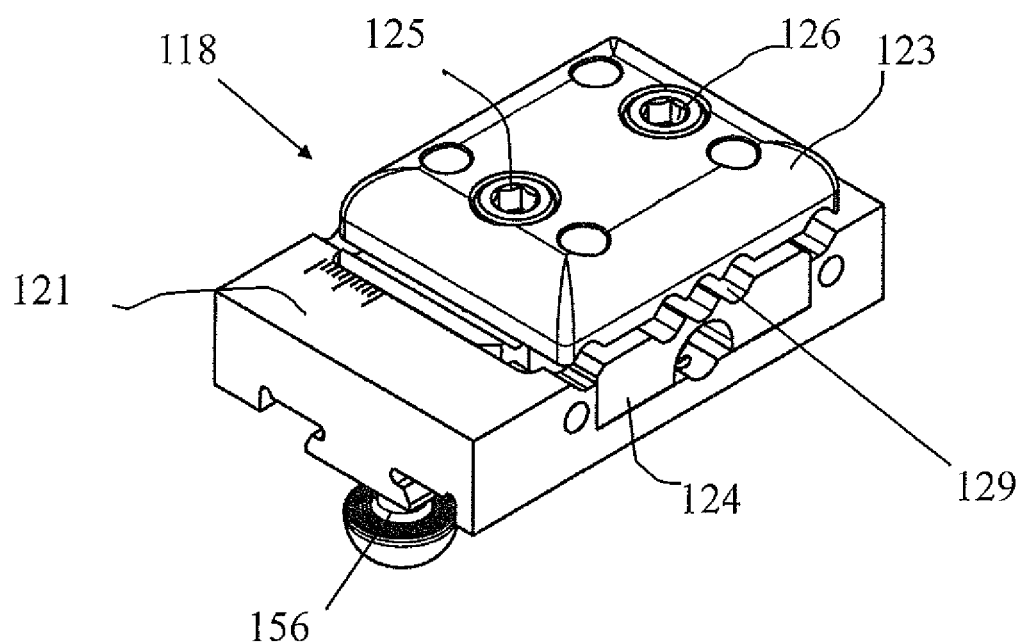
FIG. 15 is an axonometric view of a clamp of the orthopaedic device of FIG. 14.
Figure 16:
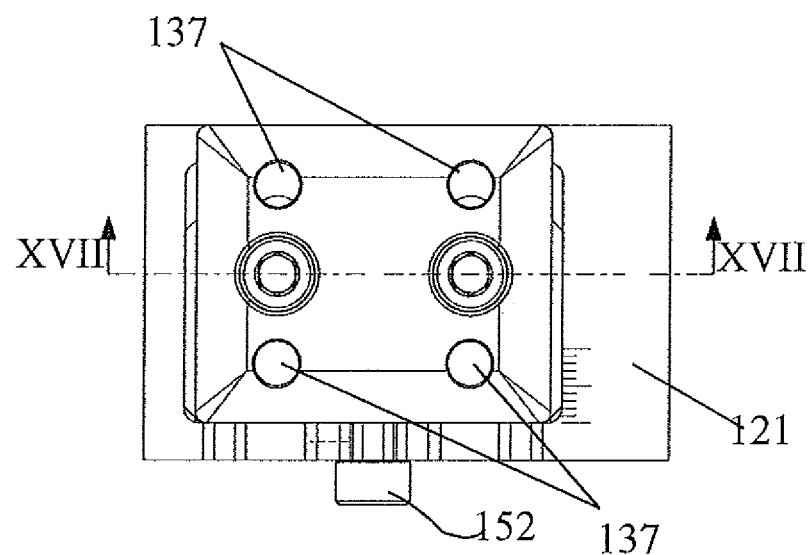
FIG. 16 is a plan view of the clamp of FIG. 15.
Figure 17:
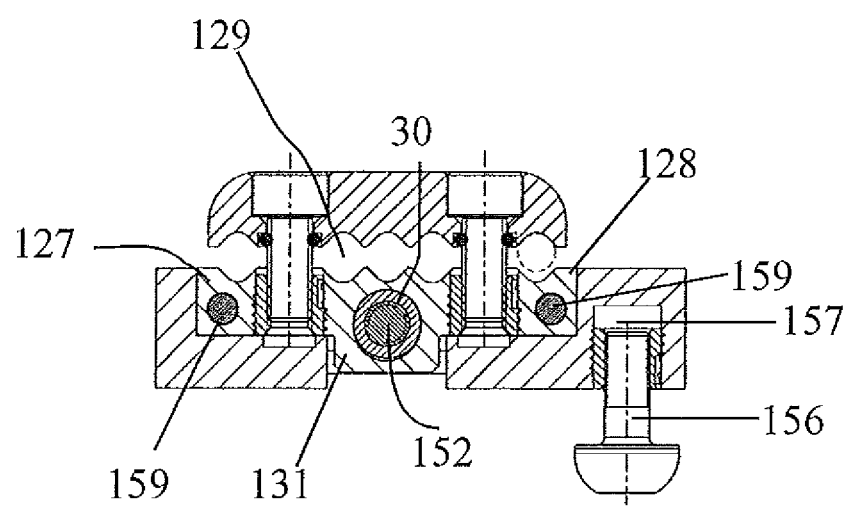
FIG. 17 is a section along the line XVII-XVII of FIG. 16.

Moreover, in some cases of bone deformities a simple angular displacement is sufficient like in this embodiment, without compensation with linear displacement, like in the following two embodiments. In particular, for small angular corrections it is not usually necessary to have correction with translation, which makes the system simpler and more cost-effective, since an angular correction can be made on the tangent where for small angle variations the translation is small (as illustrated in FIG. 14).

With reference to FIGS. 14 to 23, an orthopaedic device 110 in accordance with a further embodiment is illustrated.

In such figures, components that are the same and ones that that, have the same function already described keep the same reference numerals. Such shared components are not therefore described again in detail.

The orthopaedic device 110 comprises, mounted on a longitudinal bar 12 provided with an inverted T-shaped groove 15, and with a longitudinal hole 13, a first clamp 14 mounted onboard a support base 21, in which the longitudinal bar 12, the first clamp 14 and the support base 21 are the same as those described earlier in relation to the first embodiment. The clamp 14 supports a first group of screws 16 fixed to a first piece of bone.

The orthopaedic device 110 also comprises a second clamp 118 for a second group of osseous screws 20, housed in corresponding seats 129 of the clamp 118.

The two clamps 14, 118 are connected together by means of the compressor/distractor 58, which is described in relation to the first embodiment.

This second clamp 118, unlike the second clamp 18 of the previous embodiment, can translate in relation to the longitudinal bar 12, transversally in relation to the axis Y-Y, with a reciprocating movement when approaching and moving away from the bone 11.

In particular, the clamp 118 is mounted onboard a carriage 121, and is able to translate in relation to the carriage 121 with said reciprocating movement. Such movement is obtained through a driving screw 152, which rotates but does not translate, and in particular has the shank 152b inserted and held axially in a hole of the carriage 121, and connected through screwing to the clamp 118, as shall be described more clearly hereafter.

In particular, the second clamp 118 comprises a lower jaw 124 and an upper jaw 123, having a substantially rectangular shape, closed together by means of clamping screws 125 and 126.

Even more specifically, the lower jaw 124 of the second clamp 118 has, at the sides, respective lateral extensions 127, 128 in which transversal holes 132, 133 are made, which form shoulders 127a, 128a.

The lower jaw 124 also comprises an appendix 131 projecting towards the carriage 121. In such an appendix 131, a hole 135 is formed provided with a relative internally threaded insert 30, the same as those described earlier with reference to FIG. 12, where the driving screw 152 is screwed in.

There is also a groove 134 aligned with the hole 135 to accommodate the shank 152b of the driving screw 152.

The second clamp 118 is completed by four holes 137 formed passing between the upper jaw 123 and the lower jaw 124, and which are intended to receive the engaging pins 63 of the compressor/distractor 58.

The carriage 121 is substantially in the form of a rectangular plate-like body with short sides 121a, 121b and long sides 121c, 121d and a substantially T-shaped transversal profile, with vertical core 142, which, like the support base 21, in turn has an inverted T-shaped profile to be slidingly inserted in the groove 15 of the longitudinal bar 12.

The body of the carriage 121 has a substantially rectangular recess 130 formed in it that extends from an edge of the long side 121e up to close to the opposite side 121d, and forms a sidewall 145 on the long side 121d, and two opposite flanks 146, 147 on the short sides 121a, 121b. The aforementioned sidewall 145 carries grooves 150, which are aligned with the seats 129 of the clamp 118. On the side opposite the sidewall 145, at the flanks 146, 147, the carriage 121 also has two end stop walls 148, 149.

Figure 22:
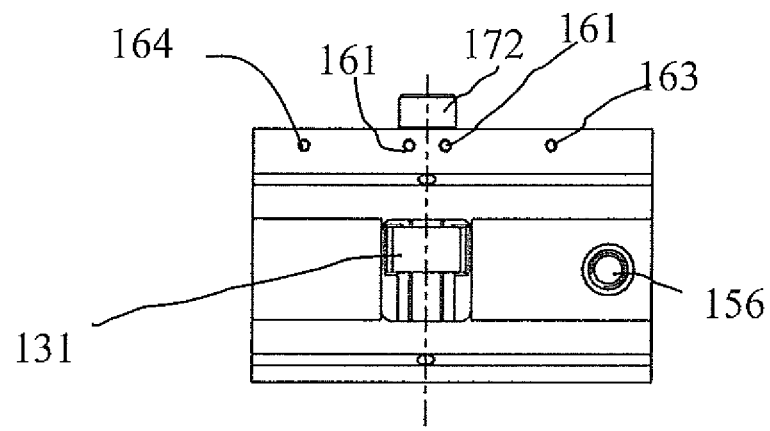
FIG. 22 is a plan view from below of the clamp of FIG. 15.

At the centre of the sidewall 145 an internally smooth hole 151 is formed, in which the shank 152b of the driving screw 152 is inserted. Such a hole 151 is aligned with a groove 153 formed at the centre of the recess 130, which is aligned with the groove 134 of the lower jaw 124 to receive the shank 152b of the driving screw 152. The carriage 121 also comprises a window 154 having a substantially rectangular shape with rounded corners, in which the aforementioned appendix 131 is received projecting from the bottom of the lower jaw 124 of the clamp 118. The arrangement of the appendix 131 in the window 154, in association with the driving screw 152 is illustrated in FIG. 22.

At the sides of the window 154 there are oval hollows 155 to receive the ends of the clamping screws 125, 126.

The carriage 121 is completed by a locking screw 156 which is inserted in a lateral hole 157 and clamps the body of the carriage 121 to the longitudinal bar 12.

In order to guide the reciprocating movement of the clamp 118, the orthopaedic device comprises two guide pins 159, having a cylindrical shape, which are inserted in the through holes 132, 133 made along the lateral extensions 127, 128 of the lower jaw 124. The two guide pins 159 have ends received in four corresponding holes 160 formed at the walls 148, 149 and on the opposite sidewall 145 of the carriage 121.

Figure 23:
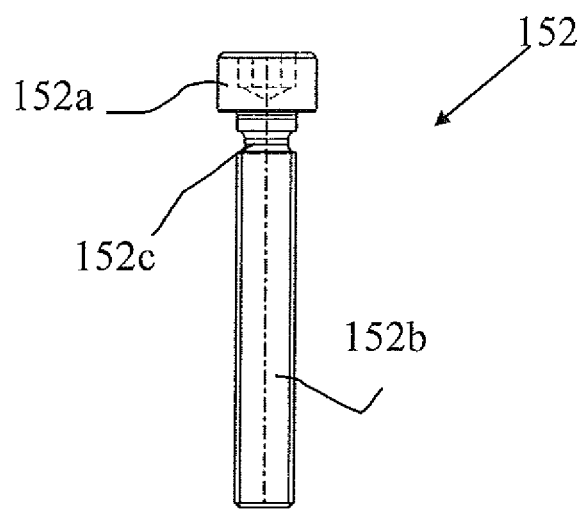
FIG. 23 is a view of a screw for the clamp of FIG. 15.

The driving screw 152 is illustrated in detail in FIG. 23, and comprises a head 152a, the aforementioned shank 152b, and a undercut 152c formed between the head 152a and the shank 152b.

The screw is inserted into the hole of the carriage 121, and into the hole of the appendix until the head abuts against the sidewall 145, so that the gorge is housed in the hole of the edge.

In order to hold the driving screw 152 in axial position, and to allow it to rotate but not translate, the orthopaedic device 110 comprises elastic or full stop pins 161 which are inserted into the sidewall 145 of the carriage 121 from below, in other words from the side of the carriage 121 facing towards the longitudinal bar 12, at the sides of the driving screw 152, and received in the undercut 152c of the screw 152.

Further elastic or full pins 163, 164 (FIG. 22) are received in the sidewall 145 to lock the guide pins 159.

The orthopaedic device 110 described up to now is used in the following way.

Initially the compressor 58 is fixed on one side by means of the engaging pins 67 of the connection element 65 to the first clamp 14, as described in reference to the first embodiment, and on the other side by means of the engaging pin 63 in one of the four holes 137 of the second clamp 118.

Initially an angular displacement of the osseous screws 16 is carried out by means of actuation of the screw 54 of the compressor 58, following the same steps described above in relation to the first embodiment.

After such an angular displacement, for example by an angle of +α (alpha) about the axis X, the piece of bone 11a connected to the screws 16 is inclined by a segment A towards the longitudinal bar 12 in relation to the bone 11, as indicated by the oblique broken line of FIG. 14.

In order to compensate for this translation of the piece of bone 11, the second clamp 118 is actuated, so as to maintain a correct alignment of the two pieces.

For this purpose, by means of a suitable tool, the driving screw 152 is actuated in one direction of rotation or in the opposite direction, this rotation without translation determining a relative movement of the lower jaw 124 in relation to the carriage 121 towards or away from the bone 11, respectively.

The displacement of the lower jaw 124 is limited by the stroke of the appendix 131 in the corresponding window 154, and by the opposite sidewall 145 and walls 148, 149.

The main advantage of the present embodiment is the possibility of compensating a given lateral displacement by means of the first clamp 14, by means of a corresponding linear translation of the second clamp.

This possibility is particularly useful in the cases of bone deformities of the knee joint of the varus-valgus type, in other words in the case of valgus deviations in which the vertical mechanical axis passes outside the knee, or in the case of varus deviations in which the vertical mechanical axis passes inside it.

Indeed, precisely in these cases of deformities, a roto-translation of the two pieces of bone becomes necessary.

A further advantage is the precision in the adjustment of the translation movement, thanks to the use of a driving screw. Indeed, in the example, for every revolution of the driving screw it is possible to obtain a displacement of 1 mm of the second clamp 118.

Advantageously, the fact that it is possible to separate the angular correction and the translation correction with two separate controls makes it simple and intuitive for the surgeon to use these clamps.

With reference to FIGS. 24 to 34 an orthopaedic device 210 in accordance with a third embodiment is now illustrated.

In such figures, components that are the same and those that have the same function already described keep the same reference numerals. Such shared components are therefore not described again in detail.

The orthopaedic device 210 comprises a first clamp 214 for a first group of screws 16 and a second clamp 18 for a second group of screws 20, removably mounted on the longitudinal bar 12.

The second clamp 18 and the longitudinal bar 12 are the same as those described earlier in the first embodiment.

The first clamp 214 is mounted onboard a support base 221, and is both angularly movable by means of rotary coupling and linearly translatable in relation to the support base 221. The support base 221 is fixed to the longitudinal bar by means of a locking screw 222.

Figure 24:
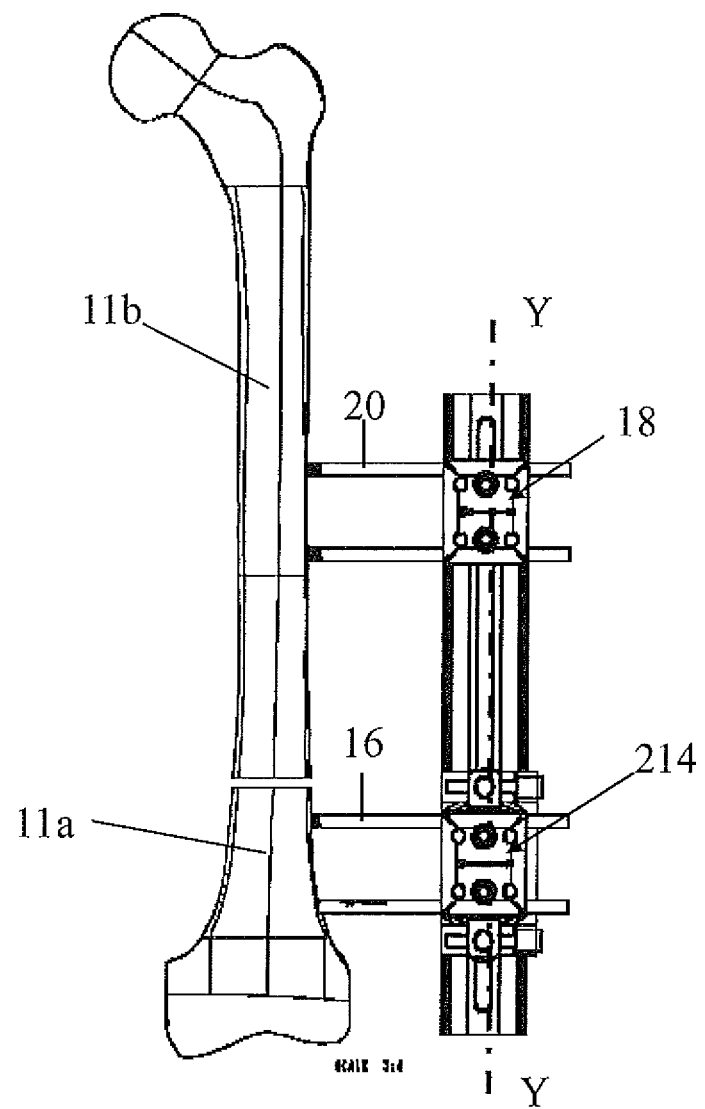
FIG. 24 is a front view of an orthopaedic device according to the invention in accordance with a third embodiment.
Figure 24A:
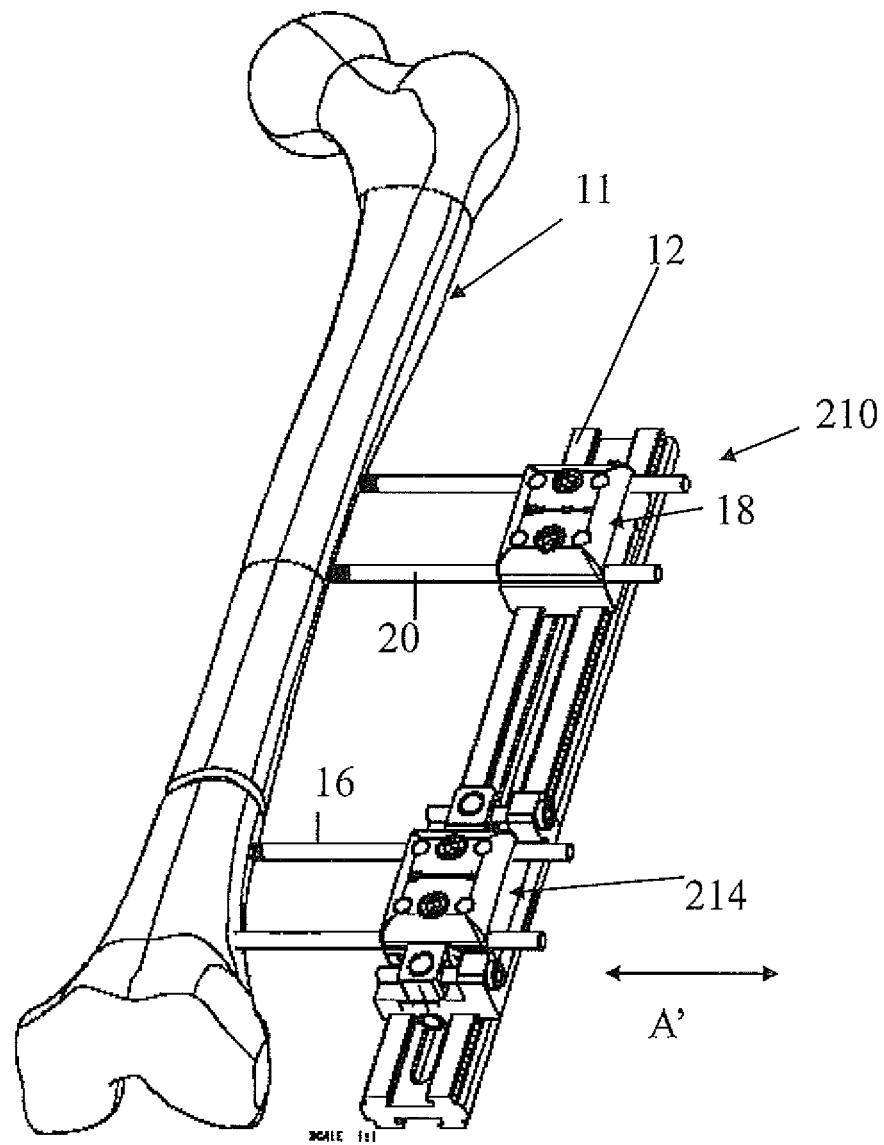
FIG. 24a is an axonometric view of the orthopaedic device according to the invention in accordance with the third embodiment.
Figure 25:
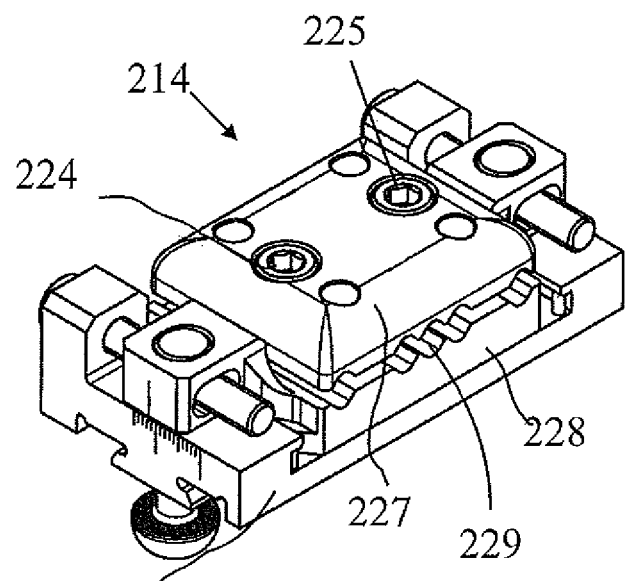
Figure 26:
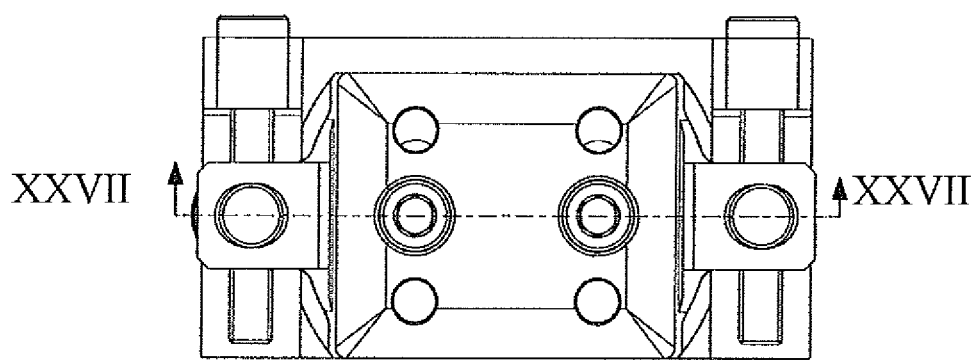
FIG. 26 is a plan view from above of the clamp of FIG. 25.
Figure 27:
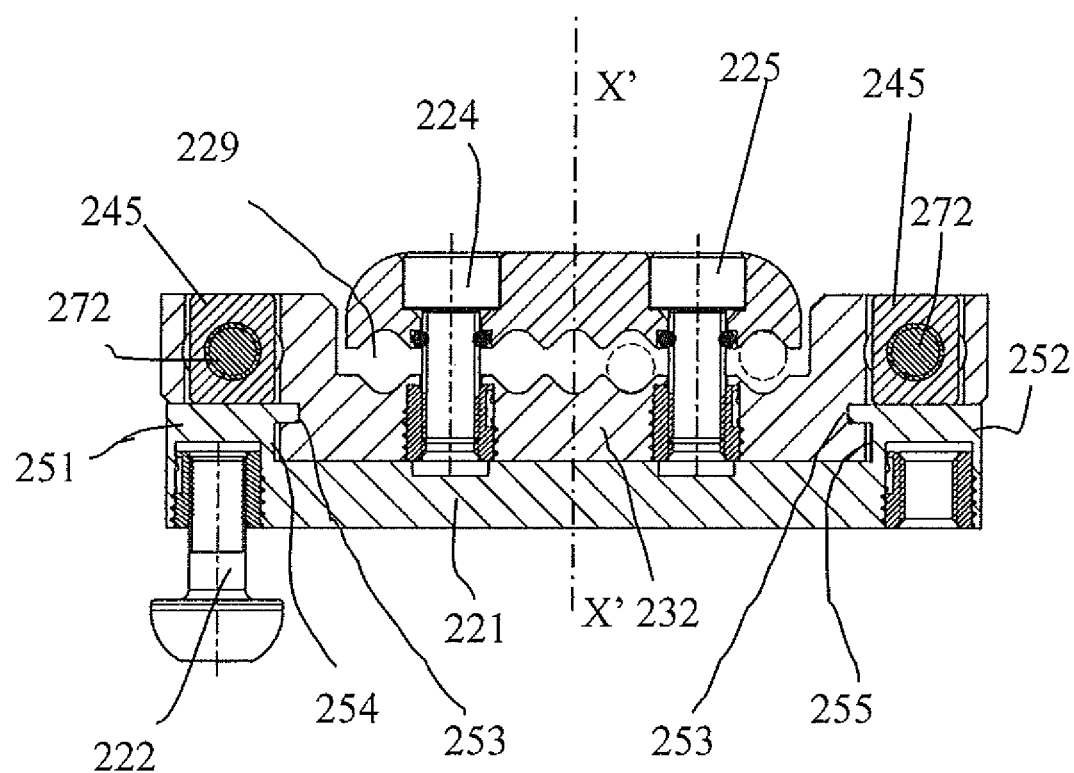
FIG. 27 is a section view along the lines XXVII-XVII of FIG. 26.
Figure 35:
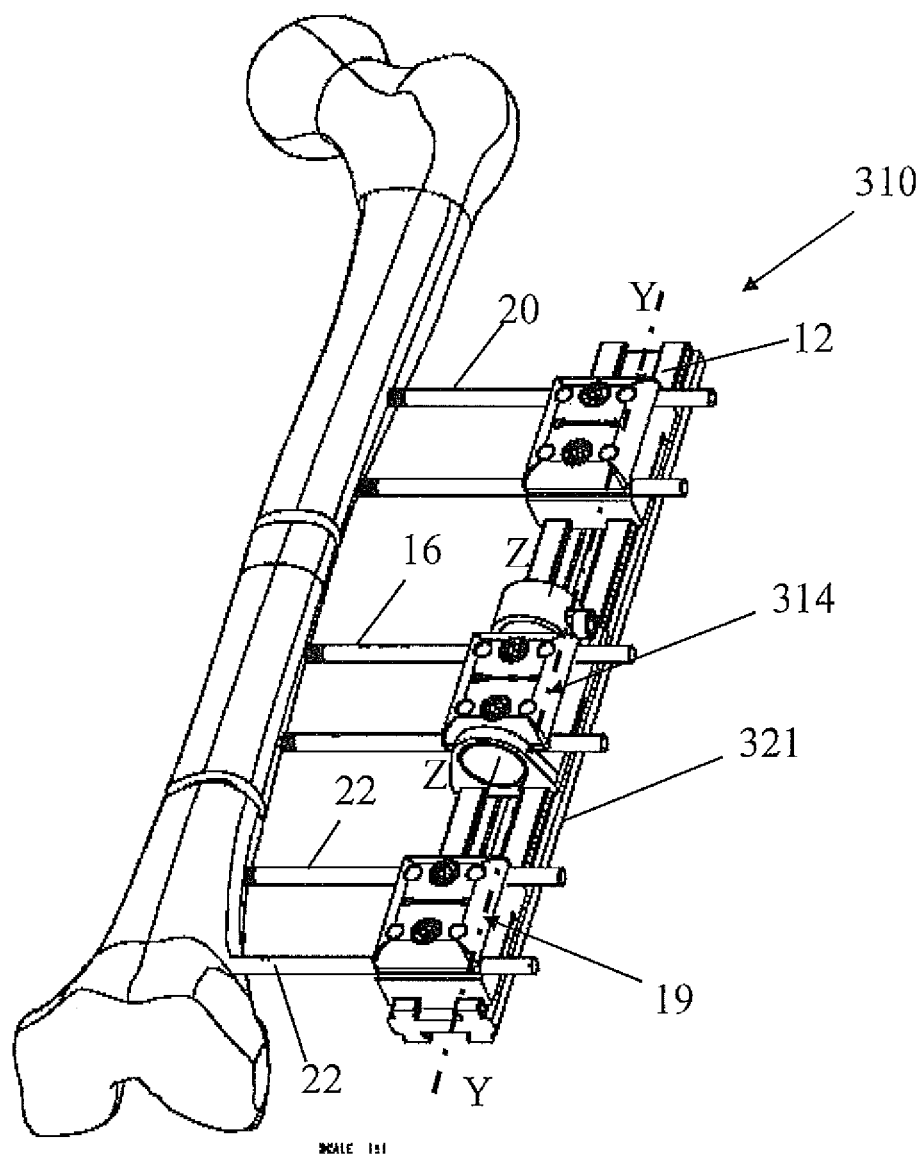
FIG. 35 is an axonometric view of an orthopaedic device according to the invention in accordance with a fourth embodiment.
Figure 36:
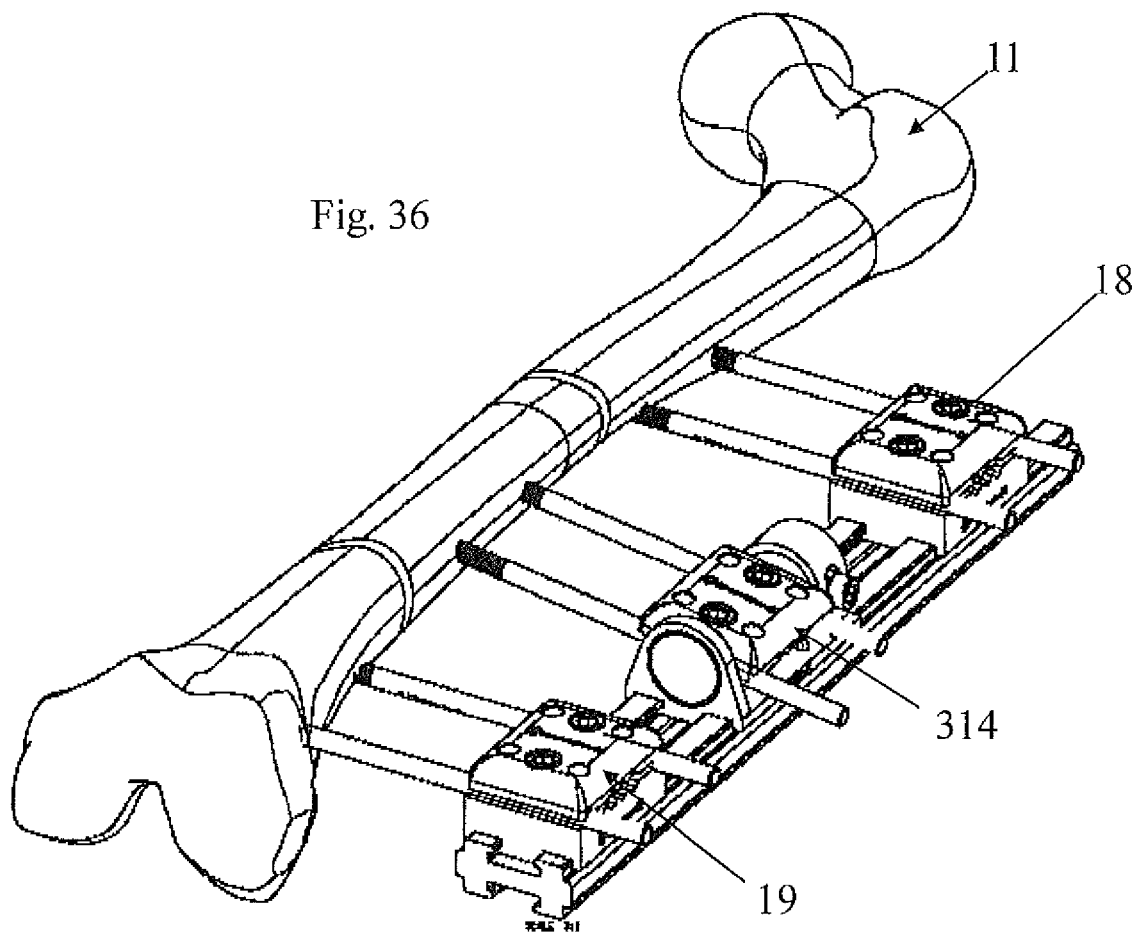
FIG. 36 is an axonometric view of the orthopaedic device of FIG. 35 in a different operating condition.
Figure 36A:
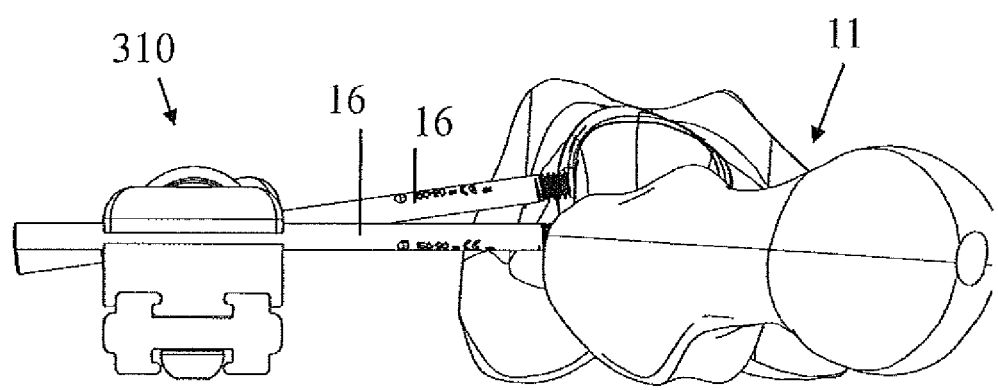
FIG. 36a is a side view of the device of FIG. 35.
Figure 37:
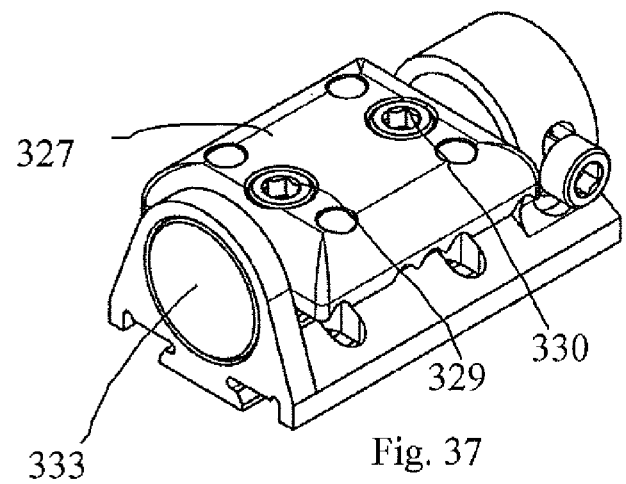
FIG. 37 is an axonometric view of a clamp for the device of FIG. 35.
Figure 38:
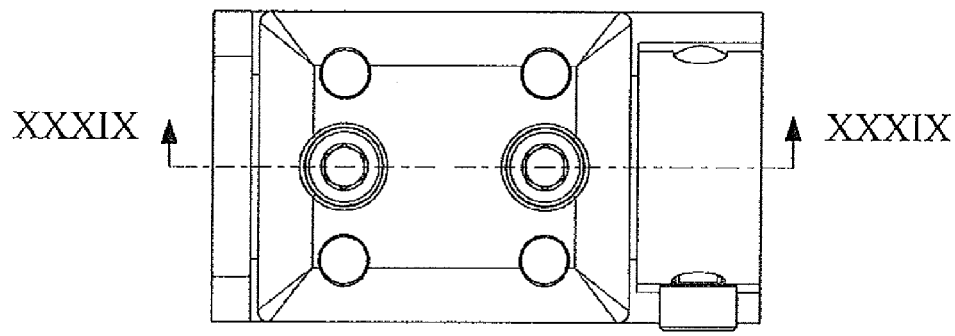
FIG. 38 is a plan view of the clamp of FIG. 37.
Figure 39:
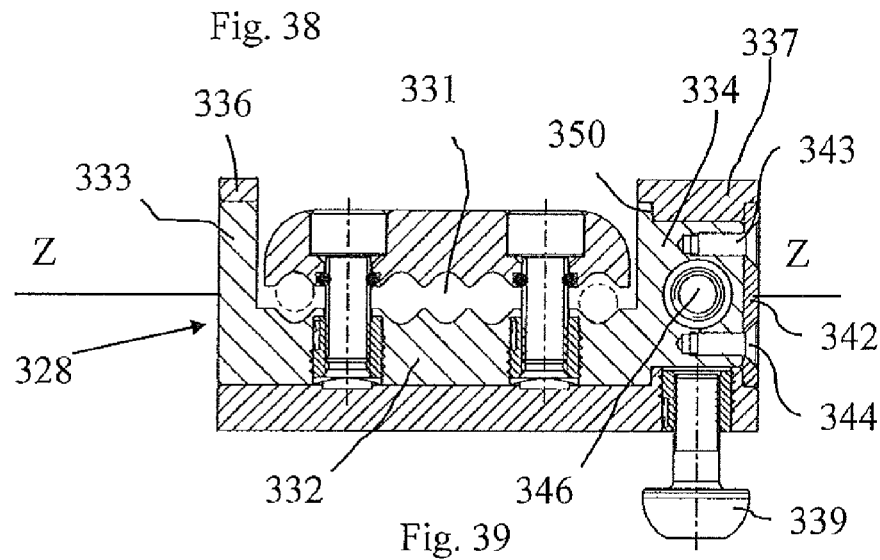
FIG. 39 is a section view along the line XXXIX-XXXIX of FIG. 38.

In other words, in the orthopaedic device 221, by means of a single clamp 214 it is possible to obtain either an angular displacement about an axis X'-X' orthogonal to the plane that passes through the osseous screws 16, 20, or a translation with reciprocating movement parallel to said plane, in a transversal direction, orthogonal to the axis Y-Y, of the longitudinal bar 12 as indicated with A' in FIG. 24.

In particular, 24. to carry out the angular displacement and the linear movement the orthopaedic device 210 comprises two driving screws 272, which, as shall be explained more clearly hereafter, rotate but do not translate, in which said driving screws 272 are actuated together in rotation with opposite directions of rotation for the angular displacement, and are actuated in rotation with the same direction of rotation to carry out the linear reciprocating movement. Consequently, in this embodiment, the compressor/distractor 58 illustrated for example in FIG. 1 is not necessary to carry out the angular displacement.

In particular, the first clamp 214 comprises an upper jaw 227 and a lower jaw 228, which are closed together by means of two locking screws 224, 225. The lower jaw 228 has a substantially U-shaped profile, visible in FIG. 33, and it comprises, in a single body, a central block 232 having a substantially rectangular shape, two lateral appendices 233, 234, which project laterally in an overhanging manner in relation to the central body 232, and on the bottom of the central block 232, at the four corners thereof, respective flaps 235, 236, 237, 238 having a cylindrical profile.

Such flaps 235, 236, 237, 238 constitute a male element of the rotary coupling for the angular displacement of the clamp 214.

In the lateral appendices 233, 234 corresponding slots 240, 241 are formed with axis orthogonal to the rotation axis X'-X', having a substantially oval profile.

At the slots 240, 241 holes 243, 244 are also formed with axis parallel to the rotation axis X'-X', also having a substantially oval profile. In such holes 243, 244 corresponding cylindrical bolts 245 are inserted, one of which is depicted in FIG. 34, having a smooth external surface and an internally threaded transversal hole. Each bolt 245 is inserted into the respective hole 243, 244, and has a threaded hole 246, in which a threaded pin is inserted, having its centre aligned in relation to the centre of the slot 240, 241.

Driving screws 272 are screwed into the holes 246 of the cylindrical bolts.

The support base 221 comprises a substantially plate-like body in which a recess 250 is formed having a substantially rectangular shape, which forms lateral edges 251, 252 at the sides. In particular, each lateral edge 251, 252 on the side facing towards the recess 250 has a segment having an inverted L-shaped profile that defines two sliding guides 254, 255 for the clamp. In particular, the projecting segment of the L-shaped profile is inserted into a matching linear groove 253 formed on the sides of the central body 232 of the lower jaw 228. The recess 250 and the two sliding guides 254, 255 defined by it act as a female element, the seat for the male element.

The support base 221 also comprises, at each lateral edge 251, 252, two vertical appendices 260, 261, which project in an overhanging manner towards the lower jaw 228, and having an internally smooth hole 268, 269 centred with the holes 246 of each bolt 245, as illustrated in FIG. 28.

In order to drive the reciprocating movement and the angular displacement, the orthopaedic device 210 comprises the aforementioned two driving screws 272 each of which is inserted in the hole 268, 269 of the vertical appendix 260, 261, and screwed into the hole 246 of the insert 245.

Each driving screw 272 has substantially the same structure as the driving screws 152 described in the second embodiment, and therefore comprises a head, a shank, and a gorge arranged between head and shank.

Also in this embodiment, to axially hold each driving screw 272, to allow it to rotate but not translate, the orthopaedic device 210 comprises elastic stop pins 280, 281 which are inserted into the vertical appendices 260, 261 of the support base 221 from the bottom, in other words from the side of the support base 221 facing towards the longitudinal bar 12, to the sides of each driving screw 272, and received in the gorge of the screw, as illustrated in FIG. 31.

The operation of the orthopaedic device 210 is the following.

The first clamp 214 is slidingly housed onboard the support base 221, in particular in the recess 250, and connected to the support base 221 by means of the driving screws 272.

The support base 221 is fixed in a given position on the longitudinal bar 12 in a distanced relationship from the second clamp 18.

In order to carry out an angular displacement the two driving screws 272 are actuated together in rotation with opposite directions of rotation. In particular, the rotation in opposite directions of the two driving screws 272 causes an angular displacement of the lower jaw 228, and consequently of the entire clamp 214.

It should be noted that the angular displacement of the lower jaw 228 of the clamp 214 in relation to the support base 221 is permitted thanks to the oval shape of the vertical holes, and of the slots 240, 242 with horizontal axis, in which the cylindrical bolts 45 are housed connected to the driving screws 272.

During the angular displacement, the lower jaw 228 rotates upon itself in the recess, and thanks to the cylindrical profile of the four flaps 235, 236, 237, 238 stability in angular displacement is ensured.

Once the angular displacement has been carried out, a translation of the first clamp 214 is carried out towards or away from the bone, to compensate for the linear displacement of the piece of bone following the angular displacement.

For this purpose, the two driving screws are screwed in the same direction of rotation thus causing a linear displacement of the lower jaw 228, and consequently of the entire clamp 214.

The same piece of bone which has subjected is subjected to linear compensating displacement.

The main advantage of the present embodiment is the possibility of carrying out a stable angular displacement of the clamp in relation to the support base, and at the same time obtaining a precise translation of the clamp. In practice, in relation to the previous embodiment, in this third embodiment, a correction in varus-valgus can be obtained with a single clamp.

The linear guides 254, 255 that as stated act as a seat for the male element, guide such an element, in the example represented by the four flaps, both during the angular displacement and during the translation without generating instability.

Like in the second embodiment, it is possible, thanks to the driving screws, to obtain a micrometric movement of 1 mm per screw turn.

With reference to FIGS. 35 to 42 a fourth embodiment of the orthopaedic device 310 according to the invention is illustrated.

In such figures, components that are the same and those that have the same function already described in the previous embodiments keep the same reference numerals. Such shared components are therefore not described again in detail.

In particular, the orthopaedic device 310 comprises a first clamp 314 for a first group of osseous screws 16, and a second clamp 18 for a second group of osseous screws 20 removably mounted on a longitudinal bar 12.

The orthopaedic device 310 comprises a third clamp 19 for a third group of screws 22, also removably mounted on the longitudinal bar 12. The second clamp 18, the third clamp 19, and the longitudinal bar 12 are the same as those described with reference to the first embodiment.

The first clamp 314 is placed onboard a support base 321, in turn mounted on the longitudinal bar 12.

In particular, the first clamp 314 is angularly movable, by means of a rotary coupling, in relation to the longitudinal bar 12 about an axis Z-Z, parallel to the axis Y-Y of the longitudinal bar 12 to allow an angular displacement of swinging type of the screws 16.

In particular, the clamp 314 comprises an upper jaw 327, and a lower jaw 328, closed together by means of locking screws 329, 330, and between which there are transversal seats 331 housing the osseous screws 16.

The upper jaw 327 comprises a plate-like body having a substantially rectangular shape. The lower jaw 328, on the other hand, is substantially C-shaped, and comprises, at the sides, a first cylindrical body 333 and a second cylindrical body 334 both with axis Z-Z. Such cylindrical bodies are joined by a central plate-like body 332, corresponding to that of the other jaw, having a substantially rectangular shape. The cylindrical bodies 333, 334 constitute a male element of the rotary coupling to allow an angular displacement about the aforementioned axis Z-Z. In the second cylindrical body 334 an internally threaded through hole 345 is formed in which a pair of inserts 30 are screwed, aligned with one another, of the type illustrated in FIG. 12, in which a locking screw 346 is screwed. As it is possible to observe from FIG. 42, the presence of two inserts 30 allows the locking screw 346 to be inserted from both sides of the clamp 314, both right and left.

Even more specifically, as can be observed from the drawings, the entire clamp 314 and the support base 321 are symmetrical in relation to the axis Z-Z, so as to be able to be inserted indistinctly on the left or right side of the long bone.

The support base 321 is substantially C-shaped, and comprises a substantially plate-like rectangular central body 335, having, at the relative sides, a first annular body 336 and a second annular body 337, both with axis Z-Z, in which cylindrical holes are formed, for loosely receiving the aforementioned first and second cylindrical body 333, 334, and which therefore act as female elements, seats for the male element.

The support base 321 is fixed to the longitudinal bar 12 by means of a clamping screw 339 screwed into a corresponding insert 30, at the second annular body 337.

The second annular body 337 also comprises, on opposite sides, a pair of slots 340, 341 having an oval shape, elongated in the direction orthogonal to the axis Z-Z, which allows the locking screw 346 to be inclined in a predetermined angular position in relation to the axis Z-Z depending on the angular position of the clamp 314.

The clamp 314 comprises a disc element 342, placed on the side of the second annular body 337 of the support base 321, and fixed by means of screws 343, 344 in the second cylindrical body 334, which acts as a lateral cover. In particular, as illustrated in FIG. 41, the lower jaw 328 is inserted laterally passing through the annular bodies 336, 337, until a radial projection 351 goes into abutment against a shoulder 350 formed on the second annular body 337 of the support base 321, and it is laterally held in such a position by means of the disc element 342.

Thereafter, by keeping the locking screw 346 in loose condition, thus partially unscrewed, the angular position of the clamp 314 is manually adjusted in relation to the other clamps 18, 19, carrying out an angular rotation of the clamp 314 about the axis Z-Z. In order to keep the clamp 314 in said desired angular position, the locking screw 346 is screwed in completely until the second cylindrical body 334 of the lower jaw is clamped in the second annular body 337 of the support base 321.

The main advantage of the orthopaedic device 310 in accordance with this embodiment is the fact that it allows an adjustment of the angular position of the screws associated with the clamp 314 about an axis substantially parallel to the axis of the longitudinal bar to adapt to a natural curvature of a bone, like in the case of a femur.

Also in this embodiment, the housing of the cylindrical bodies, in other words of the male element, in the respective annular bodies, in other words in the female element, the seat for the male element, gives high stability in rotation.

Another advantage of the orthopaedic device 310 that is offered by the symmetrical configuration of the swing clamp is the possibility of adjusting the position of the swing clamp in the same way both in a right femur and in a left femur.

The special structure of the device according to the invention, in its various embodiments, allows the threaded inserts to be housed and the stresses to be reduced so as to be able to be built even from plastic material.

Of course, a person skilled in the art can bring modifications and variants to the orthopaedic device described above, in order to satisfy contingent and specific requirements, all of which are covered by the scope of protection of the invention as defined by the following claims.

The invention claimed is:

1. An orthopedic device, comprising
a longitudinal bar;
a first clamp including a portion that holds a first plurality of osseous screws, the first clamp including a support base that is removably mountable on the longitudinal bar, and the portion being angularly movable in relation to the support base about a rotation axis;
a second clamp that holds a second plurality of osseous screws and is removably mountable on the longitudinal bar; and
a screw that sets an angular displacement of the portion of the first clamp with respect to the support base, wherein the screw:
has a longitudinal axis that is not parallel to the rotation axis,
is disposed at least partially external to the support base,
includes a first screw portion and a second screw portion,
the first screw portion includes a threaded shank,
the second screw portion includes a engagement pin, and
the first screw portion is movable along the longitudinal axis with respect to the second screw portion.

2. The orthopedic device according to claim 1, wherein the first clamp includes a cylindrical projection, and a circular hole is defined in the support base to receive the cylindrical projection.

3. The orthopedic device according to claim 2, wherein the support base comprises
a plate-like body having a substantially T-shaped transversal profile,
an upper wing providing a support for an angular movement of the first clamp, and
a vertical core having an overturned T-shaped profile that is slidingly insertable into a longitudinal groove of the longitudinal bar.

4. The orthopedic device according to claim 3, wherein the support base and the first clamp have substantially rectangular shapes with respective long sides and short sides, and
the cylindrical projection and the circular hole extend between two opposite long sides of the first clamp and of the support base.

5. The orthopedic device according to claim 4, wherein the first clamp includes a guiding slot having a shape of an arc of circle,
a center of the arc of the circle is on the rotation axis and perpendicular to a plane that passes through the first and second pluralities of osseous screws, and
the guiding slot is operable to receive a clamping screw that screws into the support base.

6. The orthopedic device according to claim 2, wherein the first clamp includes a coupling element projecting from, coaxial with, and of reduced size in relation to the cylindrical projection the coupling element having a substantially dovetail-shaped profile operable to be laterally inserted to slide into the longitudinal groove of the bar, and
the coupling element includes a hole defined therein operable to receive a clamping screw while the support base is interposed between the bar and the first clamp.

7. The orthopedic device according to claim 1, wherein the second clamp is mounted onboard a carriage by a driving screw,
the driving screw has a shank inserted into a hole defined in the carriage and connected by screwing to the second clamp,
the second clamp is translatable in relation to the carriage transversally in relation to an axis (Y-Y) of the longitudinal bar with a reciprocating movement when approaching and moving away from the bone.

8. The orthopedic device according to claim 7, wherein the second clamp includes a lower jaw and an upper jaw,
the upper jaw has a substantially rectangular shape,
the lower jaw and the upper jaw are closed between themselves by clamping screws,
the lower jaw has lateral extensions in which transversal holes are defined at sides thereof, the lateral extensions providing shoulders,
the second lower jaw includes an appendix projecting towards the carriage,
an internally threaded hole is defined in the appendix,
the driving screw is disposed in the internally threaded hole, and
the carriage includes a rectangular plate-like body having short sides, long sides and a substantially T-shaped transversal profile with a vertical core,
the vertical core has an overturned T-shaped profile operable to be slidingly inserted into a groove of the longitudinal bar, and
a substantially rectangular recess is defined in the plate-like body of the carriage that extends from one rim of the long side to near an opposed side, the recess providing a sidewall on the long side and two opposed flanks on the short sides, and the lower jaw of the second clamp is housed in the recess.

9. The orthopedic device according to claim 7, wherein the carriage includes a body having short sides and long sides, the hole defined in the carriage is an internally smooth hole defined at the center of a sidewall of the carriage, the shank of the driving screw is disposed in the internally smooth hole, the carriage includes a window defined at the center of a recess and having a substantially rectangular shape with rounded edges, the recess being defined in the body of the carriage that extends from one rim of the long side to near an opposed side, and an appendix projecting from the second clamp is disposed in the window.

10. The orthopedic device according to claim 1, wherein a lower jaw of the first clamp has a substantial C-shape, the lower jaw has a central plate-like body, the central plate-like body has a substantially rectangular shape, and at sides, a first cylindrical body and a second cylindrical body, and the first and second cylindrical bodies have axis parallel to the axis of the longitudinal bar and coinciding with the rotation axis.

11. The orthopedic device according to claim 10, wherein an internally threaded through hole is defined in the second cylindrical body, and a locking screw is disposed in the internally threaded hole.

12. The orthopedic device according to claim 11, wherein the support base has a substantial C-shape, the support base has a substantially plate-like rectangular central body on which the plate-like body of the first clamp is disposed, and the support base includes, at corresponding sides, a first annular body and a second annular body respectively having axis coinciding with the rotation axis, and cylindrical holes are respectively defined in the first annular body and the second annular body.

13. The orthopedic device according to claim 12, wherein a pair of slots having an oval shape are defined on opposite sides of the second annular body, the locking screw is disposed in at least one of the slots, and the slot is elongated in a direction orthogonal to the rotation axis.

14. The orthopedic device according to claim 13, wherein the first clamp includes a disc element disposed on a free side of the second annular body of the support base, and the first clamp is fixable by screws attached to the second cylindrical body.

15. The orthopedic device of claim 1, wherein the first clamp includes a first region that includes the first plurality of osseous screws, and the screw is disposed outside the first region.

16. The orthopedic device of claim 1, wherein the screw is coupled to the portion of the first clamp by the engagement pin inserted into a hole defined in the portion of the first clamp.

* * * * *